US012714977B2

(12) United States Patent
Koike et al.

(10) Patent No.: US 12,714,977 B2
(45) Date of Patent: Aug. 25, 2026

(54) PROPYLENE OXIDE PRODUCTION APPARATUS AND PROPYLENE OXIDE PRODUCTION METHOD

(71) Applicant: Sumitomo Chemical Company, Limited, Tokyo (JP)

(72) Inventors: Hirofumi Koike, Sodegaura (JP); Shuhei Yoshida, Tokyo (JP); Kazunori Oda, Ichihara (JP); Shoko Ikeda, Ichihara (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 952 days.

(21) Appl. No.: 17/909,596

(22) PCT Filed: Jan. 28, 2021

(86) PCT No.: PCT/JP2021/002953

§ 371 (c)(1),
(2) Date: Sep. 6, 2022

(87) PCT Pub. No.: WO2021/192592

PCT Pub. Date: Sep. 30, 2021

(65) Prior Publication Data

US 2023/0118403 A1 Apr. 20, 2023

(30) Foreign Application Priority Data

Mar. 27, 2020 (JP) ................................ 2020-057674

(51) Int. Cl.

*B01J 8/00* (2006.01)
*B01J 8/04* (2006.01)
*B01J 31/16* (2006.01)
*C07D 301/19* (2006.01)

(52) U.S. Cl.

CPC ............. *B01J 8/001* (2013.01); *B01J 8/0419* (2013.01); *B01J 8/0492* (2013.01); *B01J 31/1608* (2013.01); *C07D 301/19* (2013.01); *B01J 2208/00017* (2013.01); *B01J 2208/00539* (2013.01); *B01J 2208/00548* (2013.01); *B01J 2231/72* (2013.01)

(58) Field of Classification Search

CPC ........................................................ B01J 8/001
See application file for complete search history.

(56) References Cited

U.S. PATENT DOCUMENTS 5,849,937 A 12/1998 Jubin, Jr. et al.
6,211,388 B1 4/2001 Tsuji et al.
6,583,300 B1 6/2003 Leyshon et al.
9,221,775 B2 12/2015 Van Mourik et al.
2003/0187285 A1 10/2003 Balthsart
2010/0048925 A1 2/2010 Yamamoto et al.
2012/0130096 A1 5/2012 Crampton et al.

FOREIGN PATENT DOCUMENTS

CN 1688562 A 10/2005
CN 102401817 A 4/2012
CN 103724299 A 4/2014
CN 206002343 U 3/2017
CN 107694507 A 2/2018
EP 1551819 B1 3/2006
JP 2001526280 A * 12/2001 ........... C07D 301/19
JP 2004501906 A * 1/2004 ........... C07D 301/12
JP 2005097175 A 4/2005
JP 2005097185 A 4/2005
JP 2006513155 A 4/2006
JP 2006131562 A * 5/2006
JP 2008266304 A * 11/2008 ........... C07D 301/19
KR 20000028973 A 5/2000
RU 2655160 C2 5/2018
RU 2676691 C1 1/2019

OTHER PUBLICATIONS

Extended European Search Report issued Aug. 25, 2023 in European Application No. 21775559.4.
Int'l Search Report issued Apr. 6, 2021 in Int'l Application No. PCT/JP2021/002953.
Int'l Preliminary Report on Patentability issued Sep. 22, 2022 in Int'l Application No. PCT/JP2021/002953 with English translation.
Office Action issued Mar. 20, 2024 in RU Application No. 2022127218, with machine English translation.

* cited by examiner

*Primary Examiner* — John S Kenyon

(74) *Attorney, Agent, or Firm* — Panitch Schwarze Belisario & Nadel LLP

(57) ABSTRACT

Provided is a propylene oxide production apparatus including a switching mechanism that is capable of switching a state of each reactor between an operating state where reaction raw materials are supplied and an epoxidation reaction is performed and a non-operating state where the supply of the reaction raw materials is shut off. The propylene oxide production apparatus is capable of changing a reactor in the non-operating state one by one, and performs switching in such a way that only reactors in the operating state are connected fluidically in series or in parallel, thereby enabling supplying the reaction raw materials to the reactors in the operating state. A sampling mechanism is also provided that samples part of the reaction mixture from each discharge line that is connected to each reactor.

20 Claims, 17 Drawing Sheets

Fig.8

PEROXIDE
PROPYLENE
2
1 (1D)
1 (1A)
1 (1B)
1 (1C)
4
4
3

Fig.9A

PEROXIDE
PROPYLENE
2
1 (1D)
1 (1A)
1 (1B)
1 (1C)
4
4
3

Fig.9B

PEROXIDE
PROPYLENE
2
2
1 (1D)
1 (1A)
1 (1B)
1 (1C)
4
4
4
3

CUM SOLUTION
PROPYLENE
2
1
1
1
1
1
3
5(5a)
5(5a)
4
4
4

CUM SOLUTION
PROPYLENE
2
1
1
1
1
1
3
5(5a)
5(5a)
4
4
4
4

CUM SOLUTION
PROPYLENE
2
1
1
1
1
1
3
5(5a)
5(5a)
4
4
4
4

CUM SOLUTION
PROPYLENE
2
1
1
1
1
1
3
5 (5a)
5 (5a)
4
4
4

CUM SOLUTION
PROPYLENE
2
1
1
1
1
1
3
5 (5a)
5 (5a)
4
4
4
4

CUM SOLUTION
PROPYLENE
2
1
1
1
1
1
3
5 (5a)
5 (5a)
4
4
4

CUM SOLUTION
PROPYLENE
2
1
1
1
1
3
5 (5a)
5 (5a)
4
4
4

CUM SOLUTION
PROPYLENE
2
1
1
1
1
3
5 (5a)
4
4

CUM SOLUTION
PROPYLENE
2
1
1
1
1
3
5 (5a)
4
4
4

PROPYLENE OXIDE PRODUCTION APPARATUS AND PROPYLENE OXIDE PRODUCTION METHOD

CROSS-REFERENCE TO RELATED APPLICATIONS

This application is a Section 371 of International Application No. PCT/JP2021/002953, filed Jan. 28, 2021, which was published in the Japanese language on Sep. 30, 2021, under International Publication No. WO 2021/192592 A1, which claims priority under 35 U.S.C. § 119 (b) to Japanese Application No. 2020-057674, filed Mar. 27, 2020, the disclosure of each of which is incorporated herein by reference in its entirety.

FIELD OF THE INVENTION

The present invention relates to a propylene oxide production apparatus and a propylene oxide production method.

BACKGROUND OF THE INVENTION

As a propylene oxide production method, a method of epoxidizing propylene using a peroxide in the presence of a catalyst is known (see Patent Literatures 1 and 2). As a propylene oxide production apparatus by such a method, an apparatus including: a plurality of reactors in which a catalyst is stored; a supply line that supplies propylene and a peroxide as reaction raw materials to each reactor; a discharge line that discharges a reaction mixture containing propylene oxide from each reactor; and connection lines that connect the reactors with each other to enable supplying the reaction mixture that is discharged from each reactor and that contains the reaction raw materials to a plurality of the other reactors is known (see Patent Literature 3).

In producing propylene oxide using such a production apparatus, one or some reactors of a plurality of reactors are placed in a non-operating state where the supply of the reaction raw materials are shut off, and a plurality of the other reactors are placed in an operating state where the reaction raw materials are supplied and the epoxidation reaction is performed. Thereby, generation of propylene oxide is performed in a plurality of the reactors in the operating state.

When the generation of propylene oxide is continued in this manner, the activity of the catalyst is lowered, so that the epoxidation reaction cannot be performed efficiently. Therefore, the catalyst whose activity has been lowered (deactivated) needs to be exchanged for every reactor. Specifically, of a plurality of the reactors in the operating state, a reactor in which the catalyst has been deactivated is switched to the non-operating state, and a reactor in the non-operating state is switched to the operating state. Then, the catalyst in the reactor switched to the non-operating state is exchanged while the generation of propylene oxide is performed in a plurality of reactors in the operating state. Thereby, the catalyst can be exchanged without stopping the generation of propylene oxide, and therefore efficient operation can be performed.

However, it is difficult to grasp the time until the catalyst is deactivated for every reactor in advance, and therefore it is difficult to determine the timing of exchanging the catalyst for every reactor.

CITATION LIST

Patent Literature

Patent Literature 1: JP 2005-97175 A
Patent Literature 2: JP 2005-97185 A
Patent Literature 3: JP 2001-526280 T

SUMMARY OF THE INVENTION

Technical Problem

Accordingly, an object of the present invention is to provide a propylene oxide production apparatus and a propylene oxide production method, by which the timing of exchanging a catalyst can easily be determined for every reactor.

Solution to Problem

A propylene oxide production apparatus of the present invention is a propylene oxide production apparatus that produces propylene oxide by epoxidizing propylene using a peroxide in the presence of a titanosilicate, the apparatus including:

at least three reactors in which the titanosilicate is stored and to which propylene and the peroxide are supplied as reaction raw materials;

a supply line that supplies the reaction raw materials, which have not yet supplied to each reactor, to each reactor;

a discharge line that is connected to each reactor and that discharges a reaction mixture containing propylene oxide from each reactor;

a switching mechanism that is capable of switching a state of each reactor between an operating state where the reaction raw materials are supplied and an epoxidation reaction is performed and a non-operating state where the supply of the reaction raw materials is shut off, that is capable of changing a reactor in the non-operating state one by one, and that performs switching in such a way that only reactors in the operating state are connected fluidically in series or in parallel, thereby enabling supplying the reaction raw materials to the reactors in the operating state; and a sampling mechanism that samples part of the reaction mixture from each discharge line that is connected to each reactor.

It can be configured such that the propylene oxide production apparatus of the present invention further includes a connection line that connects reactors fluidically with each other and that supplies the reaction mixture that is discharged from one of the connected reactors and to another reactor, the reaction mixture containing the reaction raw materials, wherein the switching mechanism connects only the reactors in the operating state in series by the connection line or lines.

It can be configured such that each reactor includes: a supply part to which the reaction raw materials are supplied; and a discharge part from which the reaction mixture is discharged, and further includes thermometers that measure internal temperatures of the supply part and the discharge part respectively.

It can be configured such that each reactor includes a titanosilicate layer formed by the stored titanosilicate, and further includes a thermometer that measures an internal temperature of the titanosilicate layer.

It can be configured such that each reactor includes: a supply part to which the reaction raw materials are supplied; and a discharge part that discharges the reaction mixture, and further includes pressure gauges that measure internal pressures of the supply part and the discharge part respectively.

The at least three reactors can have approximately the same size.

It can be configured such that each reactor has a cylindrical shape, and when an inner diameter of the reactor is assumed to be D (m) and a height of the reactor is assumed to be L (m), L/D is 0.5 to 20.

Each reactor can include a pressure release valve capable of releasing internal pressure.

It can be configured such that the sampling mechanism includes a sampling line that branches from each discharge line that is connected to each reactor, and that takes in part of the reaction mixture, and an inner dimeter of the sampling line is smaller than an inner diameter of the discharge line to which the sampling line is connected.

It can be configured such that the sampling line includes a sealing part capable of forming a tightly closed region to retain the reaction mixture and has a sampling port at the sealing part.

The titanosilicate can be a silylated titanosilicate.

The titanosilicate can be a titanosilicate silylated with 1,1,1,3,3,3-hexamethyldisilazane.

The peroxide can be an organic peroxide.

The organic peroxide can be at least one selected from the group consisting of cumene hydroperoxide, ethylbenzene hydroperoxide, and tert-butyl hydroperoxide.

A propylene oxide production method of the present invention uses the above-described propylene oxide production apparatus and includes:

(1) a first step of exchanging the titanosilicate in the reactor in the non-operating state while supplying the reaction raw materials to the reactors in the operating state and performing the epoxidation;

(2) a second step of using the switching mechanism to switch the reactor in the non-operating state, in which the titanosilicate has been exchanged, to the operating state and switching one or some reactors of a plurality of the reactors in the operating state to the non-operating state, and supplying the reaction raw materials to the reactors in the operating state and performing the epoxidation; and (3) a sampling step of sampling part of the reaction mixture by the sampling mechanism and checking a deactivation status of the titanosilicate, wherein the first step and the second step are repeated, and thereby the epoxidation is 25 performed while the reactor to be placed in the non-operating state is changed one by one to exchange the titanosilicate.

A propylene oxide production method of the present invention uses the above-described propylene oxide production apparatus and has:

(1) a first step of exchanging the titanosilicate in the reactor in the non-operating state while connecting only the reactors in the operating state in series by the connection line or lines, and supplying the reaction raw materials to the reactors in the operating state and performing the epoxidation;

(2) a second step of using the switching mechanism to switch the reactor in the non-operating state, in which the titanosilicate has been exchanged, to the operating state and switching one or some reactors of a plurality of the reactors in the operating state to the non-operating state, and connecting only the reactors in the operating state in series by the connection line or lines and supplying the reaction raw materials to the reactors in the operating state and performing the epoxidation; and (3) a sampling step of sampling part of the reaction mixture by the sampling mechanism and checking a deactivation status of the titanosilicate, wherein the first step and the second step are repeated, and thereby the epoxidation is performed while the reactor to be placed in the non-operating state is changed one by one to exchange the titanosilicate.

Timing of switching one or some reactors to the non-operating state in the second step can be determined according to the deactivation status of the titanosilicate.

The propylene oxide production method of the present invention can further include a step of separating an alcohol from the reaction mixture.

It can be configured such that the second step includes a first supply step of switching the reactor in the non-operating state, in which the titanosilicate has been exchanged, to the operating state and supplying the reaction raw materials in order of propylene and subsequently the peroxide, and in the first supply step, a ratio of a total flow volume ($\beta$) of propylene supplied until the peroxide is supplied in the reactor switched from the non-operating state to the operating state to a volume ($\alpha$) of the titanosilicate stored in the reactor switched from the non-operating state to the operating state, ($\beta/\alpha$), is 5 to 6000.

In the first supply step, a titanosilicate layer outlet temperature in the reactor can be set to 40 to 150° C. when the peroxide has been supplied to the reactor and the reactor in the non-operating state has been switched to the operating state.

In the first supply step, a titanosilicate layer outlet temperature in the reactor can be set to 40 to 150° C. during supplying only propylene to the reactor.

BRIEF DESCRIPTION OF DRAWINGS

FIG. 8 is a schematic diagram showing a state after switching the connection state of reactors in the operating state from the state in FIG. 7B in the propylene oxide production apparatus of the same embodiment.

FIG. 9A is a schematic diagram showing the connection state of reactors in the operating state in the propylene oxide production apparatus of the same embodiment.

FIG. 9B is a schematic diagram showing a state after switching the connection state of reactors in the operating state from the state in FIG. 9A.

DETAILED DESCRIPTION OF THE PREFERRED EMBODIMENT

Hereinafter, a description will be given on one embodiment of the present invention, but the present invention is not limited to the following embodiment. Note that in the following drawings, the same reference sign is given to the same or corresponding parts, and the description is not repeated.

Figure 1:
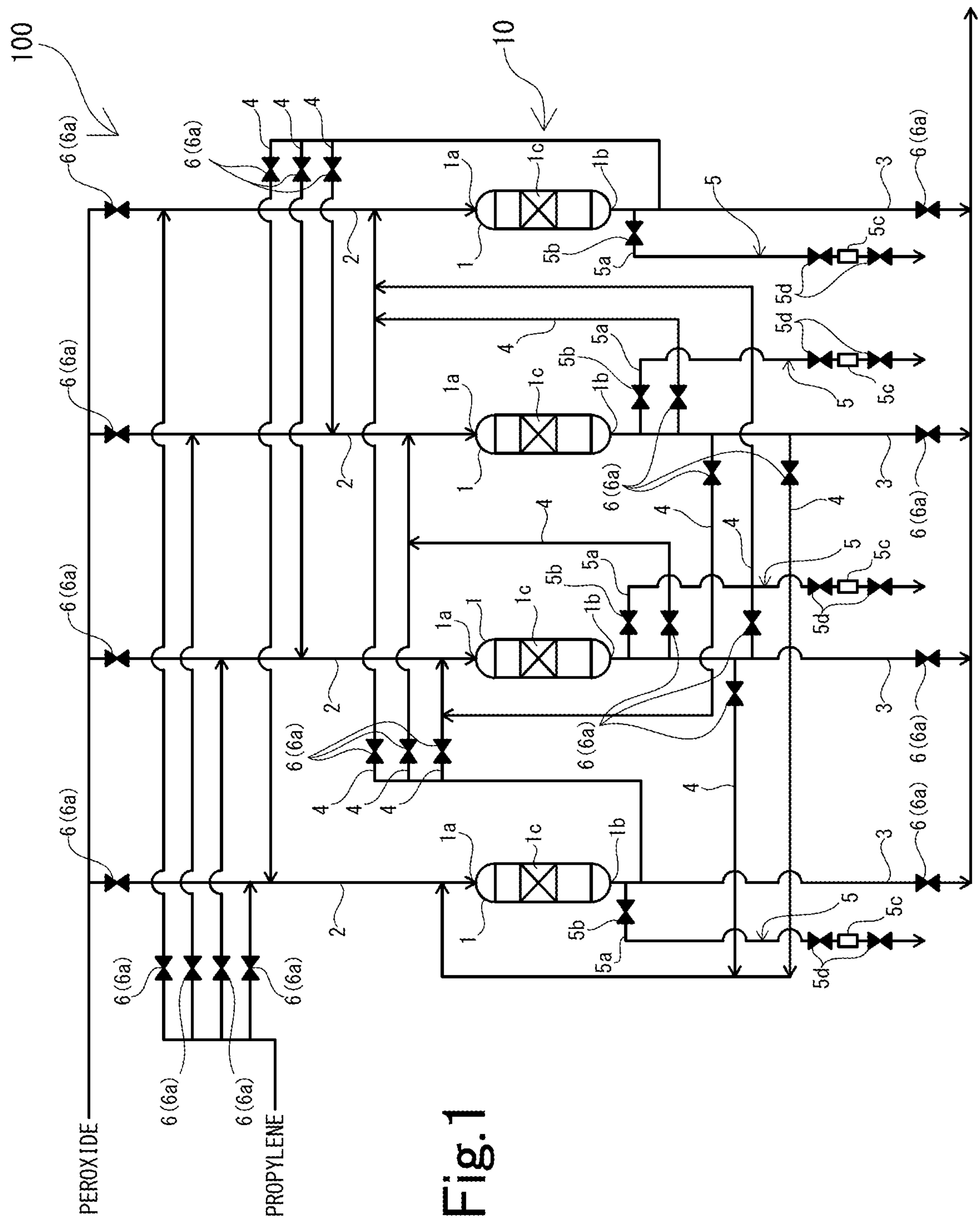
FIG. 1 is a schematic diagram showing a connection state of reactors in a propylene oxide production apparatus of one embodiment of the present invention.

A propylene oxide production apparatus (hereinafter, also simply referred to as "production apparatus") 100 of the present embodiment produces propylene oxide by epoxidizing propylene using a peroxide in the presence of a titanosilicate, as shown in FIG. 1.

Specifically, the production apparatus 100 of the present embodiment includes: four reactors 1 in which the titanosilicate is stored as a catalyst and to which propylene and the peroxide are supplied as reaction raw materials; a supply line 2 that supplies the reaction raw materials, which have not yet supplied to each reactor 1, to each reactor 1; a discharge line 3 that is connected to each reactor 1 and that discharges a reaction mixture containing propylene oxide from each reactor; and a connection line 4 that connects reactors 1 fluidically with each other and that supplies the reaction mixture that is discharged from one of the connected reactors 1 to another reactor 1, the reaction mixture containing the reaction raw materials. Further, the production apparatus 100 includes: a sampling mechanism 5 that samples part of the reaction mixture from each discharge line 3 that is connected to each reactor 1; and a switching mechanism 6 that is capable of switching a state of each reactor 1 between an operating state where the reaction raw materials are supplied and an epoxidation reaction is performed and a non-operating state where the supply of the reaction raw materials is shut off.

The sizes of the four reactors 1 are not particularly limited, and, for example, the four reactors preferably have approximately the same size. Approximately the same size means that, for example, each reactor 1 has a volume 0.5 to 1.5 times, preferably 0.6 to 1.4 times, the average value of the volume for the four reactors 1.

In addition, the shape of the reactor 1 is not particularly limited, and the reactor 1 preferably has a cylindrical shape for example. In this case, when the inner diameter (the maximum value of the diameter) of the reactor 1 is assumed to be D (m) and the height (the height of the inner space) of the reactor 1 is assumed to be L (m), L/D is preferably 0.5 to 20, more preferably 0.4 to 15.

As one aspect, given is an aspect in which the volume of each reactor 1 is 0.6 to 1.4 times the average value of the volume for four reactors 1 and L/D is 0.5 to 20. As one aspect, given is an aspect in which the volume of each reactor 1 is 0.6 to 1.4 times the average value of the volume for four reactors 1 and L/D is 0.4 to 15.

Further, each reactor 1 includes: a supply part 1*a* to which the reaction raw materials are supplied; a discharge part 1*b* from which the reaction mixture is discharged; and a titanosilicate layer 1*c* formed using the stored titanosilicate. Furthermore, each reactor 1 includes a pressure release valve (not shown) capable of releasing the internal pressure.

The supply part 1*a* is connected fluidically to the supply line 2 and the connection line 4. Thus, the supply part 1*a* is configured in such a way that at least one of the reaction raw materials (having not yet supplied to the reactor 1) which are supplied from the supply line 2 and the reaction raw materials (having been discharged from the reactor 1) which are supplied from the connection lines 4 can be supplied into the reactor 1.

The discharge part 1*b* is connected fluidically to the discharge line 3 and the connection line 4. Thus, the discharge part 1*b* is configured in such a way that the reaction mixture can be discharged to the discharge line 3 and the connection line 4.

The titanosilicate layer 1*c* can be a fluidized bed (in the form of a slurry) or a fixed bed, but is preferably a fixed bed in the case of a large-scale industrial operation.

Further, the production apparatus 100 can include thermometers (not shown) that measure the internal temperatures of the supply part 1*a* and the discharge part 1*b*.

Alternatively, the production apparatus 100 can include a thermometer (not shown) that measures the internal temperature of the titanosilicate layer 1*c*. Alternatively, the production apparatus 100 can include thermometers (not shown) that measure the internal temperatures of the supply part 1*a*, the discharge part 1*b*, and the titanosilicate layer 1*c* respectively.

When the production apparatus 100 includes the thermometers that measure the internal temperatures of the supply part 1*a* and the discharge part 1*b*, each of the supply part 1*a* and the discharge part 1*b* includes a temperature measurement part (not shown) where the thermometer is installed.

The temperature measurement parts of the supply part 1*a* and the discharge part 1*b* can include a sheath pipe part (not shown) extending inside the supply part 1*a* and the discharge part 1*b*. Then, the temperatures in the supply part 1*a* and the discharge part 1*b* can be measured through the sheath pipe parts by inserting thermocouples of the thermometers in the sheath pipe parts. Alternatively, the temperature measurement parts of the supply part 1*a* and the discharge part 1*b* can be configured in such a way that the thermocouples of the thermometers can be inserted directly inside the supply part 1*a* and the discharge part 1*b*.

When the production apparatus 100 includes a thermometer that measures the internal temperature of the titanosilicate layer 1*c*, the titanosilicate layer 1*c* includes a temperature measurement part (not shown) where the thermometer is installed. The temperature measurement part of the titanosilicate layer 1*c* can be provided at an outlet part for the reaction raw materials in the titanosilicate layer 1*c*, or one or more temperature measurement parts of the titanosilicate layer 1*c* can be provided between an inlet part and the outlet part for the reaction raw materials in the titanosilicate layer 1*c* in addition to the outlet part. Alternatively, one or more temperature measurement parts of the titanosilicate layer 1*c* can be provided between the inlet part and the outlet part for the reaction raw materials in the titanosilicate layer 1*c*.

The temperature measurement part of the titanosilicate layer 1*c* can include a protection pipe part (not shown) disposed in the titanosilicate layer 1*c*. Then, the temperature in the titanosilicate layer 1*c* can be measured through the protection pipe part by inserting thermocouples of the thermometer in the protection pipe part. Alternatively, the temperature measurement part of the titanosilicate layer 1*c* can be configured in such a way that thermocouples of the thermometer can be inserted directly in the titanosilicate layer 1*c*.

Further, the production apparatus 100 can include pressure gauges (not shown) that measure the internal pressures of the supply part 1*a* and the discharge part 1*b*. In this case, each of the supply part 1*a* and the discharge part 1*b* includes a pressure measurement part where the pressure gauge has been installed.

The amount of the titanosilicate that is stored in each reactor 1 is not particularly limited, and is, for example, preferably 10% by mass or more, more preferably 20% by mass or more, of the total amount of the titanosilicate that is used in the whole epoxidation step that is performed using three reactors 1.

The titanosilicate is not particularly limited as long as it is a known titanosilicate as an epoxidation catalyst. The titanosilicate refers to a compound in which part of Si in porous silicate (SiO2) has been substituted with Ti. The compound has a bond represented by —Si—O—Ti. Examples of the compound include compounds obtained by carrying a titanium compound on a silica carrier, compounds obtained by forming a composite with a silicone oxide by a co-precipitation method or a sol-gel method, and zeolite compounds including titanium.

More specific examples include: catalysts described in JP 2004-195379 A, JP 373184 B, and JP 3797107 B, and the like; catalysts described in US2005014960 B, CN 102311363 B, and the like; Ti-supported silica described in US2007260074 B; Ti-MCM-41 described in U.S. Pat. No. 5,783,167 B and the like; Ti-MCM-48 described in JP H-7-300312 A and the like; Ti-HMS described in Nature 368 (1994) p 321, CN 101348472 B, CN 101307039 B, CN 101279960 B, CN 102872847 B, CN 103030611 B, and the like; Ti-SBA-15 described in Chemistry of Material 14, 1657-1664, (2002) and the like; Ts-1 described in Journal of Catalysis 130, 1-8, (1991) and the like; TS-2 described in Applied Catalysis 58, L1-L4, (1991) and the like; Ti-Beta described in Journal of Catalysis 199, 41-47, (2001) and the like; Ti-ZSM-12 described in Zeolites 15, 236-242, (1995) and the like; TAPS0-5 described in Zeolites 15, 228-235, (1995) and the like; Ti-MOR described in The Journal of Physical Chemistry B 102, 9297-9303 (1998) and the like; Ti-ITQ-7 described in Chemical Communications 761-762, (2000) and the like; Ti-UTD-1 described in Zeolites 15, 519-525, (1995) and the like; and Ti-MWW and precursors thereof (for example, JP 2005-262164 A) described in Chemistry Letters 2000 p 774 and the like.

Further, a silylated titanosilicate is preferably used as the titanosilicate. The silylation treatment is performed by bringing a titanosilicate into contact with a silylating agent to convert a hydroxy group present on the surface of the titanosilicate into a silyl group.

Examples of the silylating agent include organic silanes, organic silylamines, organic silylamides and derivatives thereof, and organic silazanes, and other silylating agents.

Examples of the organic silanes include chlorotrimethylsilane, dichlorodimethylsilane, chlorobromodimethylsilane, nitrotrimethylsilane, chlorotriethylsilane, iododimethylbutylsilane, chlorodimethylphenylsilane, chlorodimethylsilane, dimethyl n-propylchlorosilane, dimethylisopropylchlorosilane, tert-butyldimethylchlorosilane, tripropylchlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane, methoxytrimethylsilane, dimethoxydimethylsilane, trimethoxymethylsilane, ethoxytrimethylsilane, diethoxydimethylsilane, triethoxymethylsilane, trimethoxyethylsilane, dimethoxydiethylsilane, methoxytriethylsilane, ethoxytriethylsilane, diethoxydiethylsilane, triethoxyethylsilane, methoxytriphenylsilane, dimethoxydiphenylsilane, trimethoxyphenylsilane, ethoxytriphenylsilane, diethoxydiphenylsilane, triethoxyphenylsilane, dichlorotetramethyldisiloxane, 3-cyanopropyldimethylchlorosilane, 1,3-dichloro-1,1,3,3-tetramethyldisiloxane, and 1,3-dimethoxy-1,1,3,3-tetramethyldisiloxane.

Examples of the organic silylamines include N-trimethylsilylimidazole, N-tert-butyldimethylsilylimidazole, N-dimethylethylsilylimidazole, N-dimethyl-n-propylsilylimidazole, N-dimethylisopropylsilylimidazole, N-trimethylsilyldimethylamine, N-trimethylsilyldiethylamine, N-trimethylsilylpyrrole, N-trimethylsilylpyrrolidine, N-trimethylsilylpiperidine, 1-cyanoethyl(diethylamino)dimethylsilane, and pentafluorophenyldimethylsilylamine.

Examples of the organic silylamides and derivatives thereof include N,O-bis(trimethylsilyl) acetamide, N,O-bis (trimethylsilyl)trifluoroacetamide, N-(trimethylsilyl) acetamide, N-methyl-N-(trimethylsilyl) acetamide, N-methyl-N-(trimethylsilyl)trifluoroacetamide, N-methyl-N-(trimethylsilyl) heptafluorobutyramide, N-(tert-butyldimethylsilyl)-N-trifluoroacetamide, and N,O-bis (diethylhydrosilyl)trifluoroacetamide.

Examples of the organic silazanes include 1,1,1,3,3,3-hexamethyldisilazane, heptamethyldisilazane, 1,1,3,3-tetramethyldisilazane, 1,3-bis(chloromethyl)-1,1,3,3-tetramethyldisilazane, 1,3-divinyl-1,1,3,3-tetramethyldisilazane, and 1,3-diphenyl-1,1,3,3-tetramethyldisilazane.

Examples of other silylating agent include N-methoxy-N,O-bis(trimethylsilyl)trifluoroacetamide, N-methoxy-N,O-bis(trimethylsilyl) carbamate, N,O-bis(trimethylsilyl) sulfamate, trimethylsilyl trifluoromethanesulfonate, and N,N'-bis(trimethylsilyl) urea.

A preferred silylating agent is an organic silazane, more preferably 1,1,1,3,3,3-hexamethyldisilazane.

The supply line 2 is connected fluidically to the supply part 1*a* of each reactor 1. In addition, the supply line 2 is configured in such a way that propylene and the peroxide, which are the reaction raw materials, can be supplied in a mixed state or separately from each other to the reactor 1.

Furthermore, the supply line 2 includes temperature regulating means (not shown) that regulates the temperature of the reaction raw materials. The temperature regulating means is not particularly limited, and, for example, a heat exchanger, a heater, a cooler, or the like can be used.

The discharge line 3 is connected fluidically to the discharge part 1*b* of each reactor 1. In addition, the discharge line 3 is formed in such a way as to branch from the connection line 4. Furthermore, the discharge line 3 is configured in such a way that the reaction mixture that is discharged from each reactor 1 is not supplied to the other reactors 1. In other words, the discharge line 3 discharges the reaction mixture outside the region where the epoxidation of propylene is performed by the reactor 1 (specifically, such as a distillation apparatus that separates a generated alcohol from the reaction mixture).

The connection line 4 is connected fluidically to the discharge part 1*b* of the one of the reactors 1 connected by the connection line 4 and the supply part 1*a* of another reactor 1. In the present embodiment, each reactor 1 is connected to all the other reactors 1 by the connection lines 4. Thereby, the production apparatus is configured in such a way that the reaction mixture (specifically, the reaction raw materials contained in the reaction mixture) that is discharged from each reactor 1 can be supplied to all the other reactors 1. In addition, the connection line 4 is formed in such a way as to branch from the discharge line 3. Furthermore, the connection line 4 includes temperature regulating means (not shown) that regulates the temperature of the reaction mixture flowing in the connection line 4. The temperature regulating means is not particularly limited, and for example, a heat exchanger, a heater, a cooler, or the like can be used.

The sampling mechanism 5 includes: a sampling line Sa that branches from each discharge line 3 that is connected to each reactor 1 and that takes in part of the reaction mixture; and a sampling valve 5*b* that enables taking the reaction mixture into the sampling line 5*a*. The inner diameter of each sampling line 5*a* is preferably smaller than the inner diameter of the discharge line 3 to which the sampling line 5*a* is connected. Further, the sampling line 5*a* includes a sealing part 5*c* capable of forming a tightly closed to retain the reaction mixture, and a sampling port (not shown) is formed at the sealing part 5*c*. Specifically, the sampling line 5*a* includes sealing valves 5*d* on the upstream side and the downstream side in the flow direction of the reaction mixture in such a way that the sealing part 5*c* is interposed between the sealing valves 5*d*, and when the two sealing valves 5*d* are closed, thereby the tightly closed region is formed.

The switching mechanism 6 is capable of changing the reactor 1 in the non-operating state one by one and performs switching in such a way that only reactors 1 in the operating state are connected fluidically in series or in parallel, thereby enabling supplying the reaction raw materials to the reactors 1 in the operating state. Specifically, the switching mechanism 6 is composed of a plurality of switching valves 6*a* that open and close the supply lines 2, the discharge lines 3, and the connection lines 4. When each switching valve 6*a* is opened or closed, thereby the reactor 1 in the non-operating state can be changed one by one, and switching can be performed in such a way that only the reactors 1 in the operating state are connected fluidically in series or in parallel and the reaction raw materials can be supplied to the reactors 1 in the operating state.

Figure 2A:
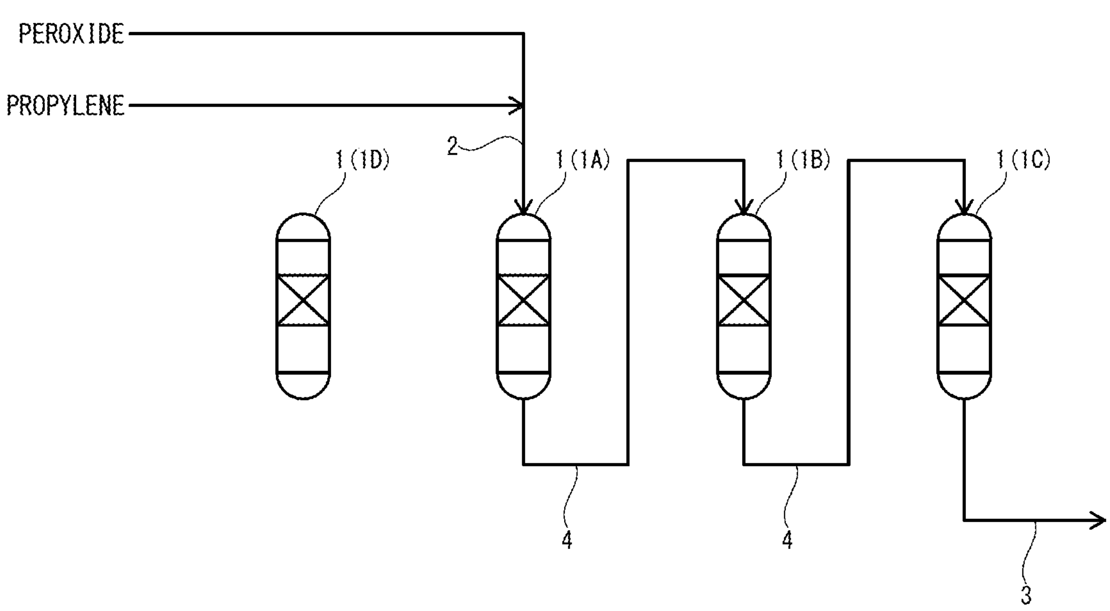
FIG. 2A is a schematic diagram showing a connection state of reactors in an operating state in the propylene oxide production apparatus of the same embodiment.

Next, a description will be given on the epoxidation step of epoxidizing propylene using the production apparatus 100 that is configured as described above. As shown in FIG. 2A, in performing the epoxidation step in the present embodiment, the switching mechanism 6 is used in such a way that one reactor 1 (hereinafter, also referred to as "the fourth reactor 1D") is placed in the non-operating state, and the other three reactors 1 (hereinafter, also referred to as "the first reactor 1A, the second reactor 1B, and the third reactor 1C") are placed in the operating state, and only the reactors 1 in the operating state (the first reactor 1A, the second reactor 1B, and the third reactor 1C) are connected in series by the connection lines 4. Then, the reaction raw materials are supplied to the reactors 1 connected in series which are in the operating state, and the epoxidation step is performed.

Specifically, the reaction raw materials are supplied from the supply line 2 to the first reactor 1A that is positioned foremost among the first to third reactors 1A to 1C connected in series. Thereby, propylene is epoxidized in the first reactor 1A and propylene oxide is generated, and the reaction mixture containing the propylene oxide is discharged to the connection line 4 from the first reactor 1A. When the epoxidation reaction is newly performed in the first reactor 1A, the supply of the reaction raw materials to the first reactor 1A is preferably performed in order of propylene and subsequently the peroxide and then performed by mixing propylene and the peroxide.

The reaction mixture discharged from the first reactor 1A is supplied to the second reactor 1B connected to the first reactor 1A by the connection line 4. In the reaction mixture discharged from the first reactor 1A, propylene and the peroxide, which are the reaction raw materials, are contained. Therefore, when the reaction mixture discharged from the first reactor 1A is supplied to the second reactor 1B, thereby propylene in the reaction mixture is epoxidized in the second reactor 1B and propylene oxide is generated.

The reaction mixture discharged from the second reactor 1B is further supplied to another reactor 1C (hereinafter, also referred to as "the third reactor 1C") connected to the second reactor 1B by the connection line 4. Thereby, propylene in the reaction mixture discharged from the second reactor 1B is epoxidized in the third reactor 1C and propylene oxide is generated. Then, the reaction mixture containing propylene oxide is discharged to the discharge line 3 from the third reactor 1C.

As described above, in the present embodiment, the reaction raw materials supplied from the supply line 2 passes through a plurality of reactors 1 (specifically, passes through the first reactors 1A to the third reactors 1C successively), and thereby the epoxidation step is performed.

Note that after the epoxidation step, a step of separating and recovering unreacted propylene from the reaction mixture in the discharge line 3 to recycle the unreacted propylene as the reaction raw material for the epoxidation step can further be performed. Distillation can be used as a method of separating and recovering unreacted propylene. In the distillation, conditions under which propylene easily vaporizes are usually used. Conditions for the distillation change depending on the temperature and the composition of the reaction solution (the reaction mixture) that is supplied to a distillation column. For example, usually, the pressure in the distillation column is preferably 0 to 5 MPa, more preferably 0 to 3 MPa, in terms of gauge pressure. In addition, the column top temperature is preferably −50 to 150° C., more preferably −30 to 140° C. The column bottom temperature is preferably 50 to 200° C., more preferably 80 to 200° C. Furthermore, a method of distilling propylene in a stepwise manner using a plurality of distillation columns can be used.

Unreacted propylene separated and recovered in this manner can be mixed with propylene to be newly supplied and supplied to an epoxidation reactor.

The temperature for the epoxidation reaction in each reactor 1 is, for example, preferably 0 to 200° C.; the temperature is preferably 25 to 200° C. from the viewpoint of reaction rate and economical use of a catalyst; and the temperature is preferably 40 to 150° C. from the viewpoint of reaction selectivity. The temperature is a temperature that is measured at the outlet part for the reaction raw materials in the titanosilicate layer 1*c* in the reactor 1 (hereinafter, also referred to as "titanosilicate layer outlet temperature). When the temperature for the epoxidation reaction is in the above-described ranges, a favorable reaction rate is obtained, and therefore the amount of a catalyst necessary for obtaining a desired reaction quantity can be reduced. In addition, when the temperature for the epoxidation reaction is in the above-described ranges, lowering the reaction selectivity can be suppressed. Thereby, the generation amount of a compound having a carbon number of 4 in particular is reduced, and therefore loss of active ingredients in removing this substance and energy necessary in removing this substance can be reduced.

The pressure in each reactor 1 during the epoxidation reaction is preferably adjusted in such a way that the reaction mixture can be retained to be in a liquid state. The pressure in each reactor 1 is not particularly limited, and is, for example, preferably 100 to 10000 kPa. Note that the pressure in each reactor 1 is calculated as the difference between the internal pressure of the supply part 1*a* of each reactor 1 and the internal pressure of the discharge part 1*b* of each reactor 1.

The temperature of the reaction mixture in the discharge part 1*b* of the first reactor 1A is not particularly limited, and is, for example, preferably 90° C. or higher, more preferably 100° C. or higher. The temperature is obtained by measuring the internal temperature of the discharge part 1*b* of the first reactor 1A with the thermometer.

In view of heat generation by the epoxidation reaction, the temperature of the reaction mixture in the discharge part 1*b* of the first reactor 1A can be controlled by, for example, adjusting at least one of the temperature of the reaction raw materials in the supply part 1*a* of the first reactor 1A (the reaction raw materials which are supplied from the supply line 2 to the reactor 1) and the temperature in the first reactor 1A (specifically, the titanosilicate layer outlet temperature). The temperature of the reaction mixture in the supply part 1*a* of the first reactor 1A is a temperature that is measured at the temperature measurement part included in the supply part 1*a* of the first reactor 1A, and the titanosilicate layer outlet temperature in the first reactor 1A is a temperature that is measured at the temperature measurement part of the titanosilicate layer 1*c*.

The temperature of the reaction mixture in the discharge part 1*b* of the third reactor 1C is preferably lower than 140° C., more preferably 139° C. or lower, still more preferably 138° C. or lower. Here, there is a possibility that the reaction mixture contains, as an impurity, methyl formate that is generated together with propylene oxide, but by setting the temperature of the reaction mixture in the discharge part 1*b* of the third reactor 1C to the above-described ranges, the methyl formate concentration in the reaction mixture can be reduced.

Further, the temperature of the reaction mixture in the discharge part 1*b* of the third reactor 1C is preferably 115° C. or higher, more preferably 117° C. or higher, still more preferably 120° C. or higher, from the viewpoint of improving the rate of the epoxidation reaction. The temperature is obtained by measuring the internal temperature of the discharge part 1*b* of the third reactor 1C with the thermometer.

The temperature of the reaction mixture in the discharge part 2*b* of the third reactor 1C can be controlled by regulating at least one of the temperature of the reaction mixture in the supply part 1*a* of the third reactor 1C and the temperature in the third reactor 1C (specifically, the titanosilicate layer outlet temperature in the third reactor 1C). The temperature of the reaction mixture in the supply part 1*a* of the third reactor 1C is a temperature that is measured at the temperature measurement part included in the supply part 1*a* of the third reactor 1C, and the titanosilicate layer outlet temperature in the third reactor 1C is a temperature that is measured at the temperature measurement part of the titanosilicate layer 1*c*.

In addition, the difference obtained by subtracting the temperature of the reaction mixture in the supply part 1*a* of the third reactor 1C from the temperature of the reaction mixture in the discharge part 1*b* of the third reactor 1C is preferably 30° C. or lower, more preferably 15° C. or lower.

The peroxide that is the reaction raw material for the epoxidation step is not particularly limited, and, for example, hydrogen peroxide, an organic peroxide, or the like can be used. The organic peroxide is not particularly limited, and, for example, at least one selected from the group consisting of cumene hydroperoxide, ethylbenzene hydroperoxide, and tert-butyl hydroperoxide can be used, and cumene hydroperoxide in particular is preferably used.

When cumene hydroperoxide is used as the peroxide, the molar ratio of propylene to cumene hydroperoxide (propylene/cumene hydroperoxide) is not particularly limited, and is, for example, preferably 2/1 to 50/1. When the molar ratio is 2/1 or more, the epoxidation can be performed at a favorable reaction rate, and therefore the epoxidation reaction can efficiently be performed. When the molar ratio is 50/1 or less, the supply amount of propylene to the reactor 1 to be excessive can be suppressed, and therefore the energy necessary in the step of recovering and recycling propylene can be suppressed.

The epoxidation reaction in each reactor 1 can be performed in a liquid phase using a solvent. Preferably, the solvent is a liquid under the temperature and pressure during the epoxidation reaction and is substantially inactive to the reaction raw materials and the reaction products. For example, as the solvent, a substance present in a peroxide solution that is supplied from the supply line 2 can be used. Specifically, when the peroxide is ethylbenzene hydroperoxide or cumene hydroperoxide, ethylbenzene or cumene present in the peroxide solution that is supplied from the supply line 2 can be used as the solvent. In addition, examples of the solvent other than these include monocyclic aromatic solvents (specifically, such as benzene, toluene, chlorobenzene, and ortho-dichlorobenzene), and alkanes (specifically, such as octane, decane, and dodecane).

The content of propylene oxide in the reaction mixture that is obtained through the epoxidation step in each reactor 1 is preferably 1 to 31% by mass, more preferably 1 to 23% by mass.

When cumene hydroperoxide is used as the peroxide, the reaction mixture (which is supplied to the reactor 1 by the connection line 4 and which is discharged from the discharge line 3) contains propylene oxide and cumyl alcohol. The content of cumyl alcohol in the reaction mixture that is obtained through the epoxidation step in each reactor 1 is preferably 5 to 80% by mass, more preferably 5 to 60% by mass, still more preferably 5 to 40% by mass. Here, cumyl alcohol means 2-phenyl-2-propanol.

Note that after the above-described epoxidation step, a step (hereinafter, also referred to as "alcohol separation step") of separating an alcohol (specifically, cumyl alcohol in the case where cumene hydroperoxide is used as the peroxide) from the reaction mixture (which is discharged from the discharge line 3) can be performed. By performing the alcohol separation step, crude propylene oxide in which the alcohol has been separated from the reaction mixture (which is discharged from the discharge line 3) can be obtained. The reaction mixture that is an object of the alcohol separation step can be one obtained by separating unreacted propylene after the epoxidation step.

Examples of the method of separating the alcohol in the alcohol separation step include a method of using a distillation column (preferably a plurality of distillation columns). In such a method, the pressure in the distillation column is preferably 100 to 5000 kPa, more preferably 100 to 3000 kPa. In addition, in such a method, the column top temperature is preferably −50 to 150° C., more preferably 0 to 130° C. In this case, the column bottom temperature is preferably 50 to 230° C., more preferably 60 to 210° C.

The content of propylene oxide in crude propylene oxide obtained by performing the alcohol separation step is not particularly limited, and is, for example, preferably 99% by mass or more per 100% by mass of crude propylene oxide.

An alcohol-converting step of converting the alcohol separated through the alcohol separation step into another compound can be performed. Examples of the alcohol-converting step include:

- a step of subjecting the alcohol to hydrogenolysis in the presence of a catalyst to obtain a hydrocarbon;
- a step of dehydrating the alcohol in the presence of a catalyst and subsequently reacting a resultant product with hydrogen to obtain a hydrocarbon; and
- a step of reacting the alcohol and a peroxide in the presence of a catalyst to obtain a dialkyl peroxide.

When the alcohol is cumyl alcohol, the hydrocarbon is cumene. When the alcohol is cumyl alcohol, the dialkyl peroxide is dicumyl peroxide. In other words, when the separated alcohol is cumyl alcohol for example, the alcohol-converting step is a step of converting cumyl alcohol into cumene and/or dicumyl peroxide.

In one aspect, the alcohol-converting step includes: a step of dehydrating, in the presence of a catalyst, cumyl alcohol in a cumyl alcohol-containing residual mixture obtained through the alcohol separation step to obtain a α-methylstyrene-containing mixture (hereinafter, referred to as "dehydration step"); and a step of bringing the α-methylstyrene-containing mixture obtained through the dehydration step and hydrogen into contact with each other in the presence of a catalyst to react α-methylstyrene in the mixture with hydrogen, thereby obtaining a cumene-containing conversion mixture (hereinafter, referred to as "hydrogenation step").

In another aspect, the alcohol-converting step is a step of bringing a cumyl alcohol-containing residual mixture obtained through the alcohol separation step and hydrogen into contact with each other in the presence of a catalyst to react cumyl alcohol in the residual mixture with hydrogen, thereby obtaining a cumene-containing conversion mixture (hereinafter, referred to as "hydrogenolysis step").

Hereinafter, a description will be given on the case where the alcohol-converting step includes the dehydration step and the hydrogenation step.

Examples of the catalyst which is used in the dehydration step (hereinafter, referred to as "dehydration catalyst") include acids such as sulfuric acid, phosphoric acid, and p-toluenesulfonic acid, and metal oxides such as activated alumina, titania, zirconia, silica alumina, and zeolite. From the viewpoint of improving the reaction efficiency, the catalyst is preferably a solid catalyst, more preferably activated alumina.

The dehydration reaction in the dehydration step is usually performed by bringing cumyl alcohol and the dehydration catalyst into contact with each other. In one embodiment, the hydrogenation reaction in the hydrogenation step is performed following the dehydration reaction, and therefore cumyl alcohol and the dehydration catalyst can be brought into contact with each other in the presence of hydrogen. The dehydration reaction can be carried out in a liquid phase in the presence of a solvent. The solvent has to be substantially inactive to the reaction raw materials and the products. The solvent can be a substance present in a cumyl alcohol-containing residual mixture to be used. For example, when the cumyl alcohol-containing residual mixture contains cumene, this cumene can be used as the solvent, and another solvent does not have to be used. Usually, the dehydration reaction temperature is preferably 50 to 450° C., more preferably 150 to 300° C. Usually, the dehydration reaction pressure is preferably 10 to 10000 kPa-G, more preferably 500 to 4000 kPa-G, still more preferably 1000 to 2000 kPa-G.

Examples of the catalyst which is used in the hydrogenation step (hereinafter, referred to as "hydrogenation catalyst") include catalysts containing a metal of group 10 or group 11 in the periodic table, and specific examples include nickel-containing catalysts, palladium-containing catalysts, platinum-containing catalysts, and copper-containing catalysts. From the viewpoint of suppression of nuclear hydrogenation reaction of an aromatic ring and high yield, the catalyst is preferably a nickel-containing catalyst, a palladium-containing catalyst, or a copper-containing catalyst. The nickel-containing catalyst is preferably nickel, nickel-alumina, nickel-silica, or nickel-carbon, the palladium-containing catalyst is preferably palladium-alumina, palladium-silica, or palladium-carbon, and the copper-containing catalyst is preferably copper, Raney copper, copper-chromium, copper-zinc, copper-chromium-zinc, copper-silica, or copper-alumina. These catalysts can be used singly, or a plurality of these catalysts can be used in combination.

The hydrogenation reaction in the hydrogenation step is performed by bringing α-methylstyrene and hydrogen into contact with a hydrogenation catalyst. In one embodiment, the hydrogenation reaction is performed following the dehydration reaction, but in this aspect, part of water generated in the dehydration reaction can be separated by oil-water separation or the like, or, instead of the separation, can be brought into contact with the hydrogenation catalyst together with α-methylstyrene. The amount of hydrogen necessary for the hydrogenation reaction can be equimolar to the amount of α-methylstyrene, but usually, excessive amount of hydrogen is used because hydrogen-consuming components other than α-methylstyrene are contained in the α-methylstyrene-containing mixture obtained through the dehydration step. In addition, usually, the molar ratio of hydrogen/α-methylstyrene is preferably 1/1 to 20/1, more preferably 1/1 to 10/1, still more preferably 1/1 to 3/1, because the reaction progresses more quickly as the partial pressure of hydrogen is increased more. Excessive hydrogen left after the hydrogenation reaction can be used by recycling after being separated from the reaction solution (conversion mixture). The hydrogenation reaction can be carried out in a liquid phase in the presence of a solvent or in a gas phase. The solvent has to be substantially inactive to the reaction raw materials and the products. The solvent can be a substance present in the α-methylstyrene-containing mixture. For example, when the α-methylstyrene-containing mixture contains cumene, this cumene can be used as the solvent, and another solvent does not have to be used. Usually, the hydrogenation reaction temperature is preferably 0 to 500° C., more preferably 30 to 400° C., still more preferably 50 to 300° C. Usually, the hydrogenation reaction pressure is preferably 100 to 10000 kPa-G, more preferably 500 to 4000 kPa-G, still more preferably 1000 to 2000 kPa-G.

The dehydration reaction and the hydrogenation reaction can be carried out advantageously in the form of slurry or fixed bed. In the case of large-scale industrial operation, the fixed bed is preferably used. In addition, the dehydration reaction and the hydrogenation reaction can be carried out by a reaction forms such as a batch process, a semi-continuous process, or a continuous process. Separate reactors or a single reactor can be used for the dehydration reaction and the hydrogenation reaction. The reactors for the continuous process include an adiabatic reactor and an isothermal reactor, but the adiabatic reactor is preferable because the isothermal reactor needs facilities for heat removal.

Examples of the catalyst which is used in the hydrogenolysis step (hereinafter, referred to as "hydrogenolysis catalyst") include catalysts containing a group 9, group 10, group 11, or group 12 metal in the periodic table, and specific examples include cobalt-containing catalysts, nickel-containing catalysts, palladium-containing catalysts, copper-containing catalysts, and zinc-containing catalysts. From the viewpoint of suppressing generation of by-products, the catalyst is preferably a nickel-containing catalyst, a palladium-containing catalyst, or a copper-containing catalyst. Examples of the nickel-containing catalyst include nickel, nickel-alumina, nickel-silica, and nickel-carbon, examples of the palladium-containing catalyst include palladium-alumina, palladium-silica, and palladium-carbon, and examples of the copper-containing catalyst include copper, Raney copper, copper-chromium, copper-zinc, copper-chromium-zinc, copper-silica, and copper-alumina. The hydrogenolysis reaction can be carried out in a liquid phase in the presence of a solvent or in a gas phase. The solvent has to be substantially inactive to the reaction raw materials and the products. The solvent can be a substance present in a cumyl alcohol-containing residual mixture to be used. For example, when the cumyl alcohol-containing residual mixture contains cumene, this cumene can be used as the solvent, and another solvent does not have to be used. The amount of hydrogen necessary for the hydrogenolysis reaction can be equimolar to the amount of cumyl alcohol, but usually, excessive amount of hydrogen is used because hydrogen-consuming components other than cumyl alcohol are contained in the cumyl alcohol-containing mixture obtained through the alcohol separation step. In addition, usually, the molar ratio of hydrogen/cumyl alcohol is preferably adjusted to 1/1 to 20/1, more preferably 1/1 to 10/1, still more preferably 1/1 to 3/1, because the reaction progresses more quickly as the partial pressure of hydrogen is increased more. Excessive hydrogen left after the hydrogenolysis reaction can be used by recycling after being separated from the reaction solution. Usually, the hydrogenolysis reaction temperature is preferably 0 to 500° C., more preferably 50 to 450° C., still more preferably 150 to 300° C. Usually, the hydrogenolysis reaction pressure is preferably 100 to 10000 kPa-G, more preferably 500 to 4000 kPa-G, still more preferably 1000 to 2000 kPa-G. The hydrogenolysis reaction can be carried out advantageously in the form of slurry or fixed bed. In the case of large-scale industrial operation, the fixed bed is preferably used. In addition, the hydrogenolysis reaction can be carried out by a reaction form such as a batch process, a semi-continuous process, or a continuous process.

Usually, the content of cumene in the cumene-containing conversion mixture is preferably 90% or more per 100% by mass of the cumene-containing conversion mixture.

Next, a description will be given on the method of exchanging the titanosilicate stored in each reactor 1 in the production apparatus 100 that is configured as described above.

When the titanosilicate in one reactor 1 of the three reactors in the operating state has been deactivated, the reactor 1 in which the titanosilicate has been deactivated is switched to the non-operating state and the reactor 1 already in the non-operating state is switched to the operating state by the switching mechanism 6. In addition, by the switching mechanism 6, only the reactors 1 in the operating state (specifically, the reactor 1 switched to the operating state and the reactors 1 in the operating state from the beginning) are connected in series by the connection lines 4 and the reaction raw materials are supplied to the reactors 1 in the operation state. Specifically, the reaction raw materials are supplied from the supply line 2 to the reactor 1 which is positioned foremost among the reactors connected in series, and the reaction mixture is supplied from the connection lines 4 to the other reactors 1 connected in series. Thereby, the titanosilicate stored in the reactor 1 switched to the non-operating state is exchanged while the epoxidation of propylene is performed in the reactors 1 in the operating state (that is, while the above-described epoxidation step is performed).

By repeating the above-described step, the reactor 1 to be placed in the non-operating state is changed one by one to exchange the titanosilicate. In other words, in exchanging the titanosilicate stored in each reactor 1 in the production apparatus 100, the titanosilicate in the reactor 1 to be an object of exchange is exchanged while the epoxidation of propylene is performed in a plurality of reactors 1 not subject to exchange.

Hereinafter, a more specific description will be given on the method of exchanging the titanosilicate stored in each reactor 1.

<When Titanosilicate in Third Reactor 1C has been Deactivated>

Figure 2B:
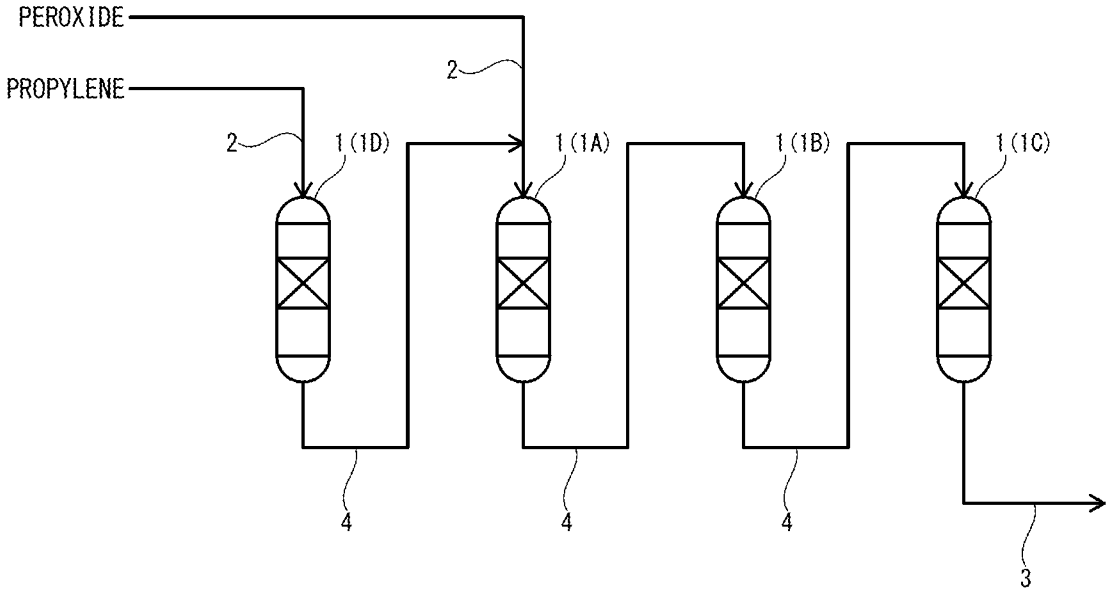
FIG. 2B is a schematic diagram showing a state after switching the connection state of reactors in the operating state from the state in FIG. 2A.

As shown in FIG. 2A, the first reactor 1A, the second reactor 1B, and the third reactor 1C are connected in series by the connection lines 4 and the epoxidation step is performed as described above with the fourth reactor 1D being in the non-operating state, and thereby when the titanosilicate in the third reactor 1C has been deactivated, switching is first performed gradually by the above-described switching mechanism 6 in such a way that propylene which is being supplied to the first reactor 1A from the supply line 2 is supplied to the fourth reactor 1D and switching is performed by the above-described switching mechanism 6 in such a way that propylene which is discharged from the fourth reactor 1 is supplied to the first reactor 1A through the connection line 4, as shown in FIG. 2B. Thereby, propylene which is discharged from the fourth reactor 1D is supplied to the first reactor 1A.

The time for supplying propylene from the fourth reactor 1D to the first reactor 1A is not particularly limited, and can be, for example, 6 hours to 720 hours, preferably 72 hours to 340 hours.

In addition, the temperature of the titanosilicate layer (the titanosilicate layer outlet temperature) during supplying propylene from the fourth reactor 1D to the first reactor 1A is not particularly limited, and is, for example, preferably 40° C. to 150° C., more preferably 40° C. to 90° C.

Furthermore, in supplying propylene from the fourth reactor 1D to the first reactor 1A, the ratio of the total flow volume (β) of propylene supplied until the peroxide is supplied to the volume (α) of the titanosilicate stored in the reactor 1 switched from the non-operating state to the operating state, (β/α), is not particularly limited, and is, for example, preferably 5 to 6000, more preferably 600 to 3000.

Figure 3A:
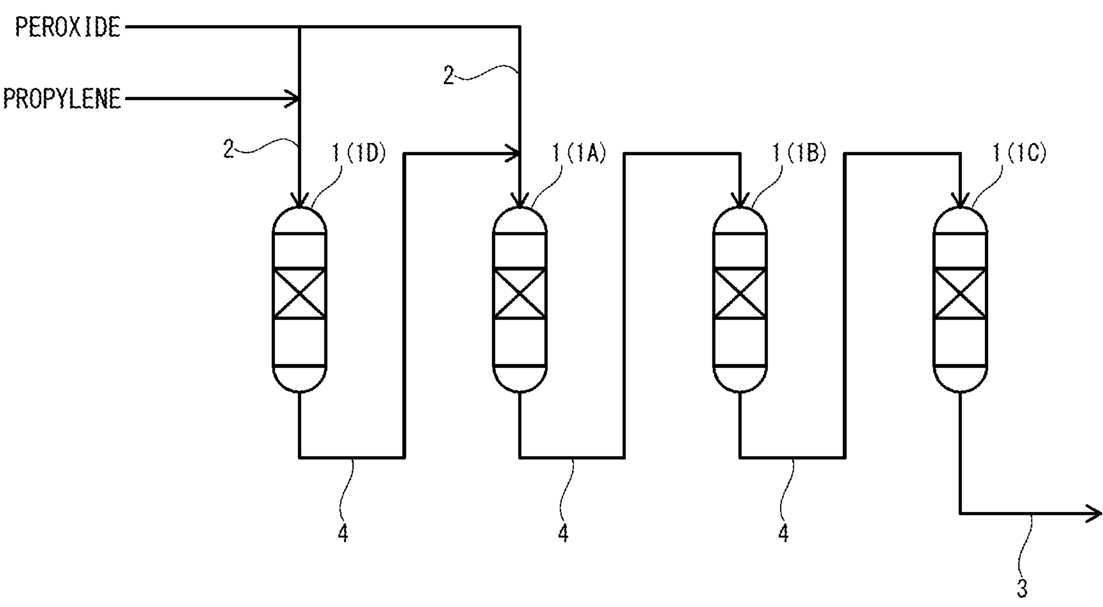
FIG. 3A is a schematic diagram showing a state after switching the connection state of reactors in the operating state from the state in FIG. 2B in the propylene oxide production apparatus of the same embodiment.

Next, as shown in FIG. 3A, switching is performed by the above-described switching mechanism 6 in such a way that part of the peroxide which has been supplied to the first reactor 1A from the supply line 2 is supplied to the fourth reactor 1D. Thereby, propylene is epoxidized in the fourth reactor 1D. Then, the reaction mixture which is discharged from the fourth reactor 1D is supplied to the first reactor 1A through the connection line 4.

The temperature of the titanosilicate layer (the titanosilicate layer outlet temperature) after the peroxide is supplied to the fourth reactor 1D is not particularly limited, and is, for example, preferably 150° C. or lower, more preferably 80° C. to 140° C.

Figure 3B:
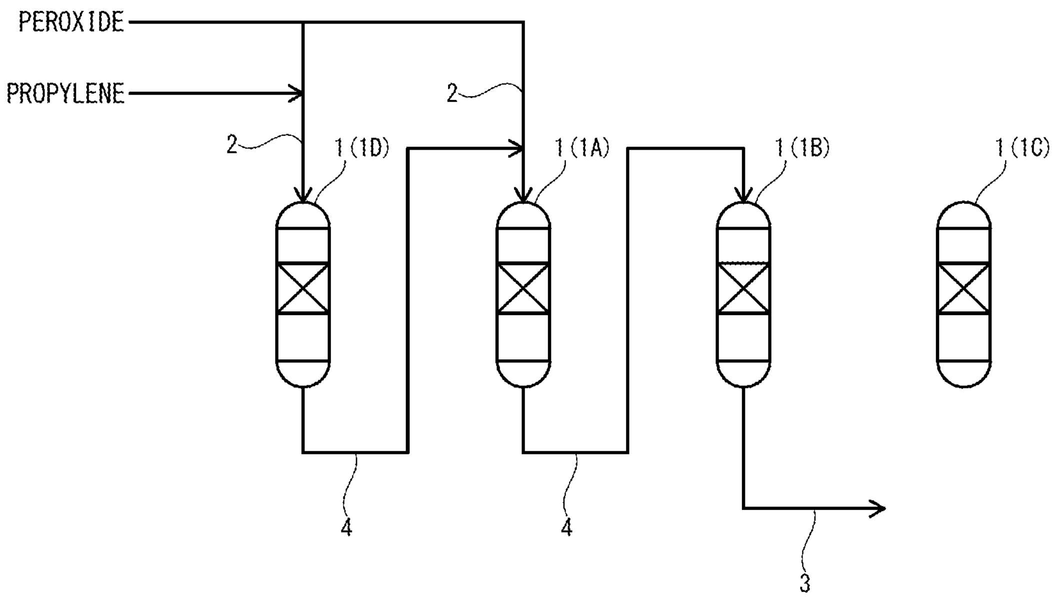
FIG. 3B is a schematic diagram showing a state after switching the connection state of reactors in the operating state from the state in FIG. 3A.

In addition, by the above-described switching mechanism 6, switching is performed in such a way that part of the reaction mixture which is supplied from the second reactor 1B to the third reactor 1C through the connection line 4 is discharged from the second reactor 1B to the discharge line 3, the discharge amount of the reaction mixture to the discharge line 3 from the second reactor 1B is gradually increased, and the supply amount of the reaction mixture from the second reactor 1B to the third reactor 1C is gradually decreased to shut off the supply of the reaction mixture from the second reactor 1B to the third reactor 1C. Thereby, the third reactor 1C is placed in the non-operating state as shown in FIG. 3B.

Figure 4:
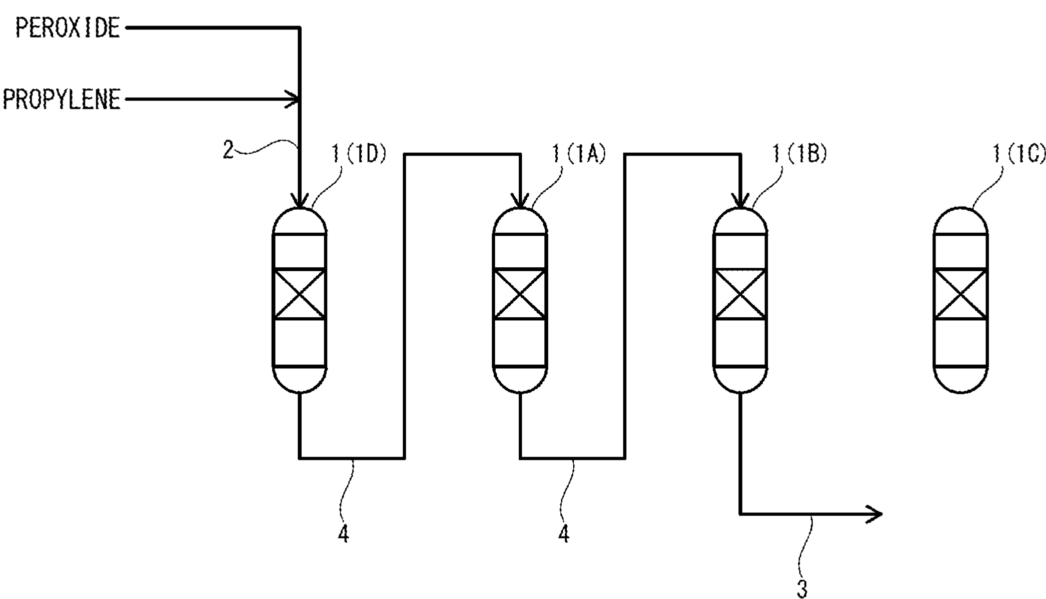
FIG. 4 is a schematic diagram showing a state after switching the connection state of reactors in the operating state from the state in FIG. 3B in the propylene oxide production apparatus of the same embodiment.

Then, by the above-described switching mechanism 6, the supply amount of the peroxide to the fourth reactor 1D from the supply line 2 is gradually increased, and the supply amount of the peroxide to the first reactor 1A from the supply line 2 is gradually decreased to shut off the supply of the peroxide to the first reactor 1A from the supply line 2 as shown in FIG. 4.

Thereby, the titanosilicate in the third reactor 1C placed in the non-operating state is exchanged with one not deactivated while the epoxidation of propylene is performed (that is, the above-described epoxidation step is performed) in the fourth reactor 1D, the first reactor 1A, and the second reactor 1B.

<When Titanosilicate in First Reactor 1A has been Deactivated>

Figure 5A:
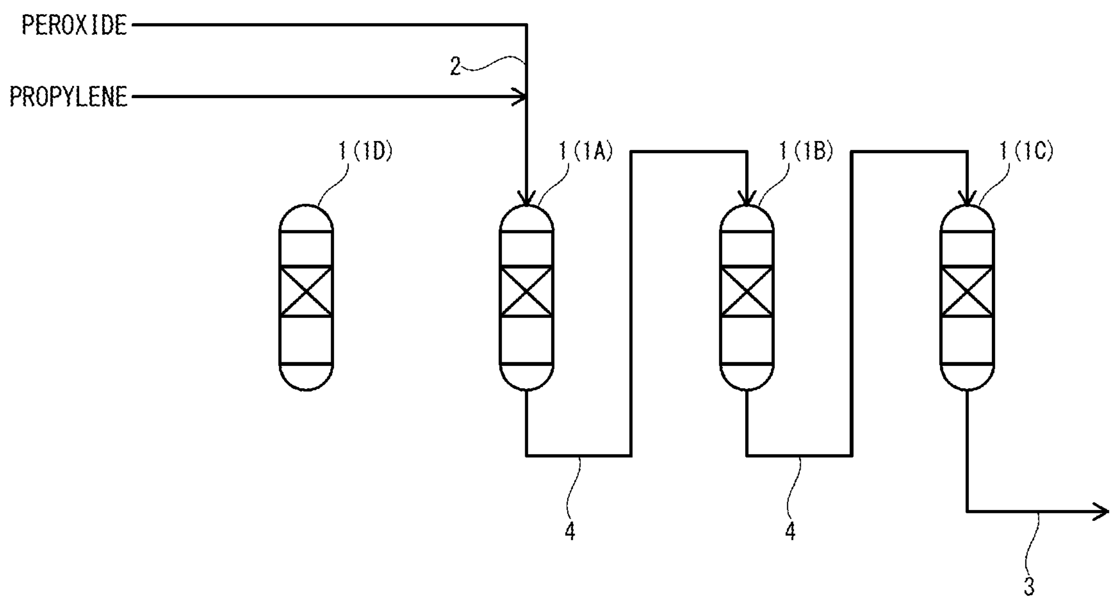
FIG. 5A is a schematic diagram showing the connection state of reactors in the operating state in the propylene oxide production apparatus of the same embodiment.
Figure 5B:
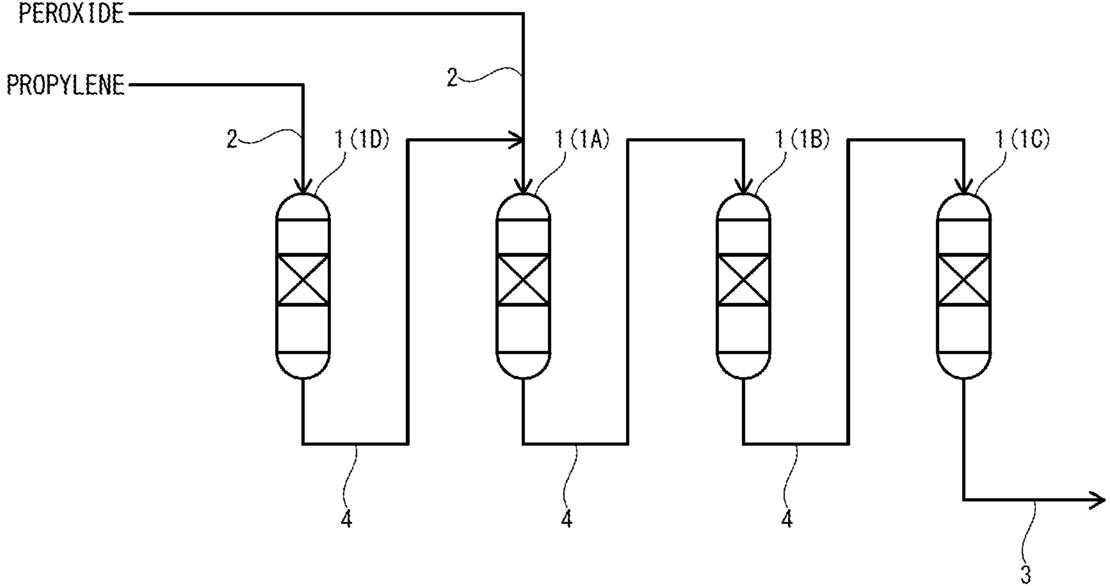
FIG. 5B is a schematic diagram showing a state after switching the connection state of reactors in the operating state from the state in FIG. 5A.

As shown in FIG. 5A, the first reactor 1A, the second reactor 1B, and the third reactor 1C are connected in series by the connection lines 4 and the epoxidation step is performed as described above with the fourth reactor 1D being in the non-operating state, and thereby when the titanosilicate in the first reactor 1A has been deactivated, switching is first performed gradually by the above-described switching mechanism 6 in such a way that propylene which is being supplied to the first reactor 1A from the supply line 2 is supplied to the fourth reactor 1D, and switching is performed by the above-described switching mechanism 6 in such a way that propylene which is discharged from the fourth reactor 1D is supplied to the first reactor 1A through the connection line 4, as shown in FIG. 5B. Thereby, propylene which is discharged from the fourth reactor 1D is supplied to the first reactor 1A.

The time for supplying propylene from the fourth reactor 1D to the first reactor 1A can be set in the same manner as described in <When Titanosilicate in Third Reactor 1C Has Been Deactivated>.

In addition, the temperature of the titanosilicate layer (the titanosilicate layer outlet temperature) during supplying propylene from the fourth reactor 1D to the first reactor 1A can be set in the same manner as described in <When Titanosilicate in Third Reactor 1C Has Been Deactivated>.

Furthermore, the ratio of the total flow volume (β) of propylene supplied until the peroxide is supplied to the volume (α) of the titanosilicate stored in the reactor 1 switched from the non-operating state to the operating state, (β/α), can be set in the same manner as described in <When Titanosilicate in Third Reactor 1C Has Been Deactivated>.

Figure 6A:
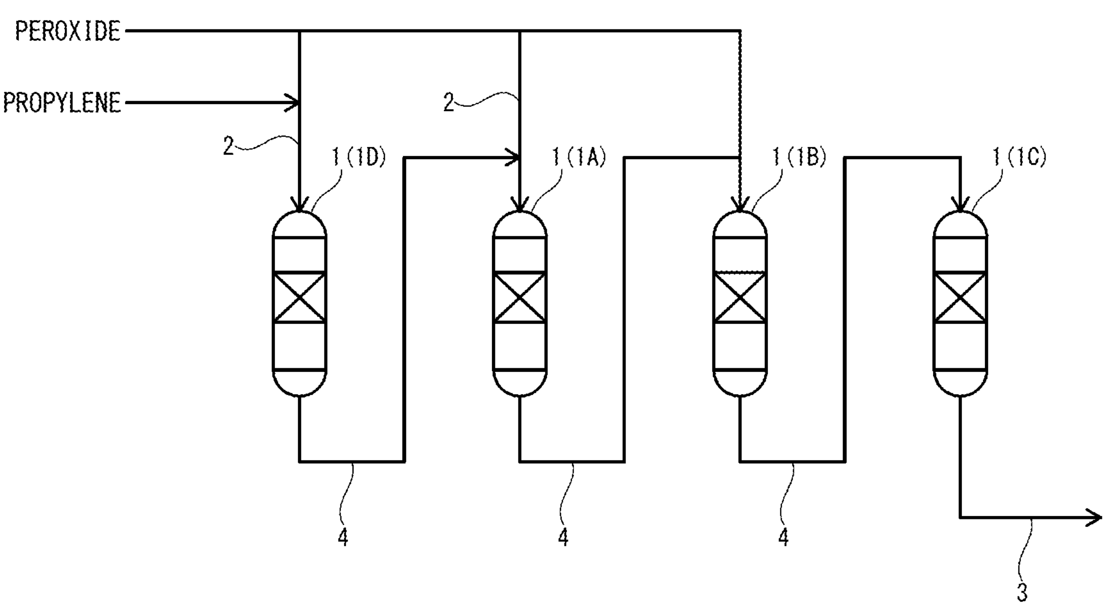
FIG. 6A is a schematic diagram showing a state after switching the connection state of reactors in the operating state from the state in FIG. 5B in the propylene oxide production apparatus of the same embodiment.

Next, as shown in FIG. 6A, switching is performed by the switching mechanism 6 in such a way that part of the peroxide which has been supplied to the first reactor 1A from the supply line 2 is supplied to the fourth reactor 1D and the second reactor 1B. Thereby, propylene is epoxidized in the fourth reactor 1D. Then, the reaction mixture which is discharged from the fourth reactor 1D is supplied to the first reactor 1A through the connection line 4.

The temperature of the titanosilicate layer (the titanosilicate layer outlet temperature) after the peroxide is supplied to the fourth reactor 1D can be set in the same manner as described in <When Titanosilicate in Third Reactor 1C Has Been Deactivated>.

Figure 6B:
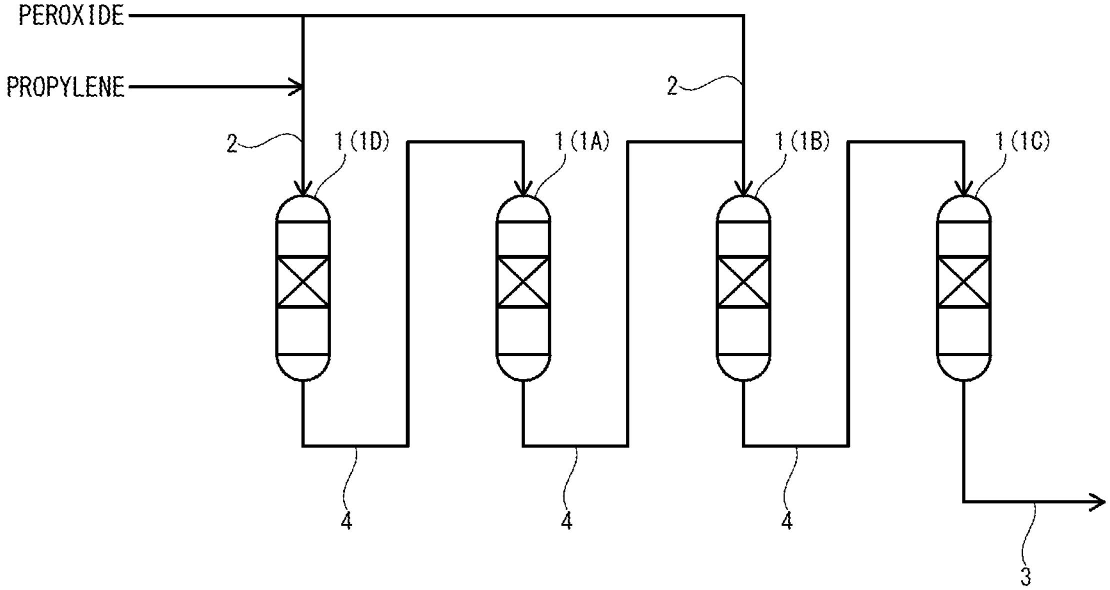
FIG. 6B is a schematic diagram showing a state after switching the connection state of reactors in the operating state from the state in FIG. 6A.

Next, by the above-described switching mechanism 6, the supply amount of the peroxide to the fourth reactor 1D and the second reactor 1B from the supply lines 2 is gradually increased, and the supply amount of the peroxide to the first reactor 1A from the supply line 2 is gradually decreased to shut off the supply of the peroxide to the first reactor 1A from the supply line 2 as shown in FIG. 6B.

Figure 7A:
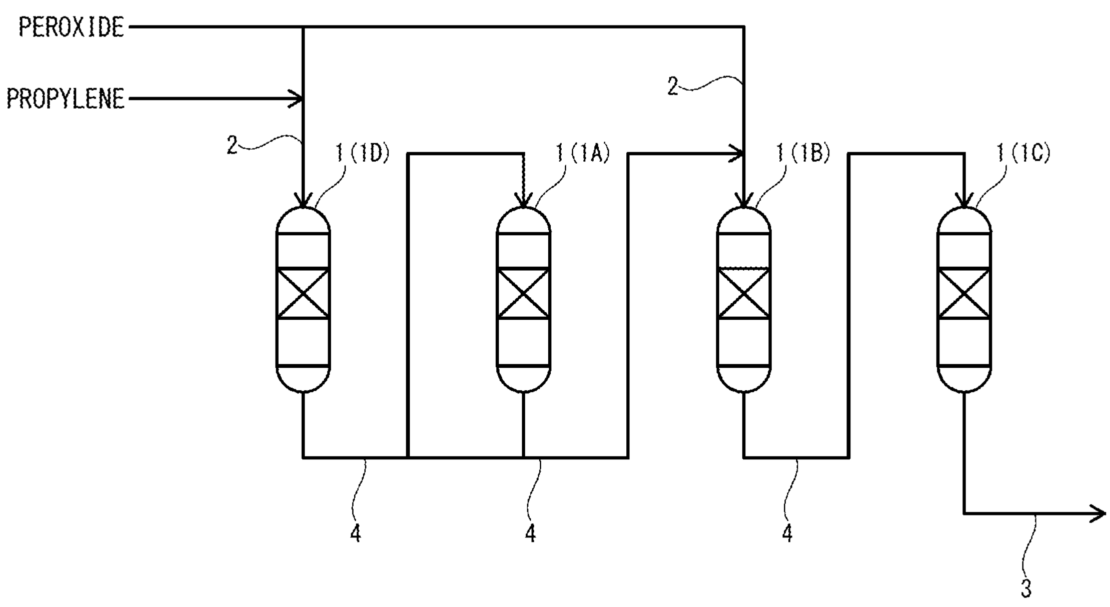
FIG. 7A is a schematic diagram showing a state after switching the connection state of reactors in the operating state from the state in FIG. 6B in the propylene oxide production apparatus of the same embodiment.
Figure 7B:
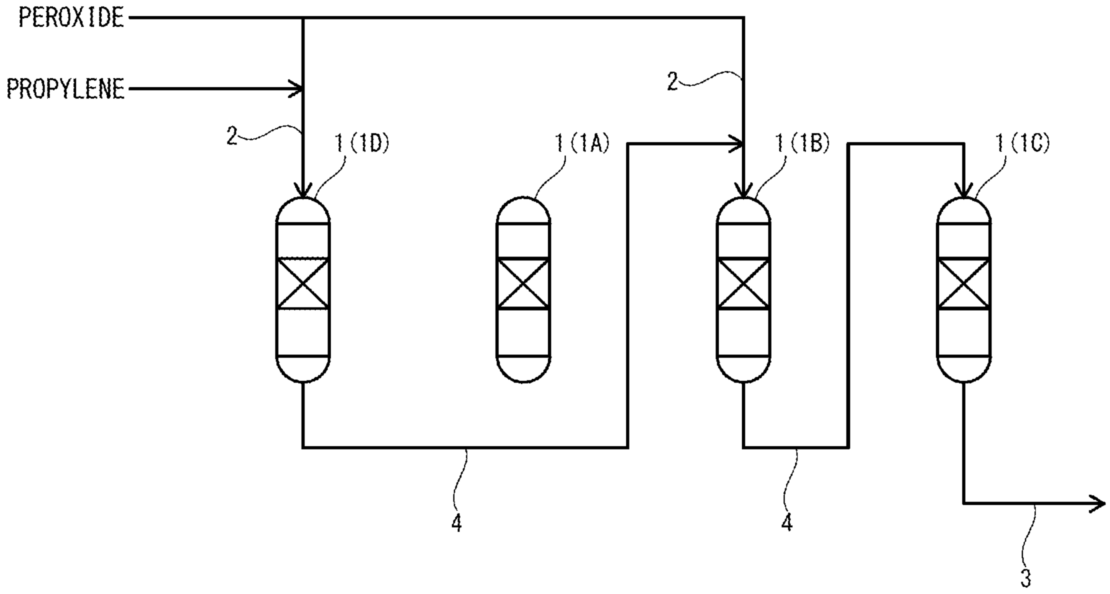
FIG. 7B is a schematic diagram showing a state after switching the connection state of reactors in the operating state from the state in FIG. 7A.
Figure 8:
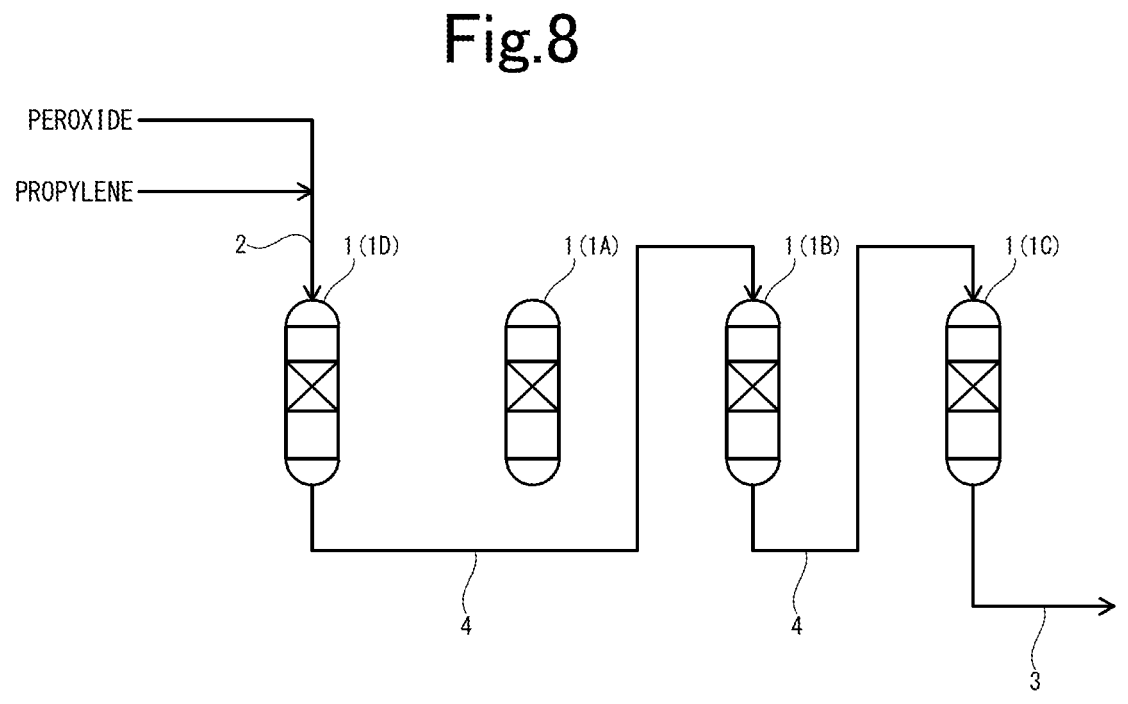

Next, as shown in FIG. 7A and FIG. 7B, by the above-described switching mechanism 6, switching is performed in such a way that the reaction mixture which is discharged from the fourth reactor 1D is supplied to the second reactor 1B through the connection line 4, the supply amount of the reaction mixture from the fourth reactor 1D to the second reactor 1B is gradually increased, the supply amount of the reaction mixture from the first reactor 1A to the second reactor 1B is gradually decreased, and further the supply amount of the reaction mixture from the fourth reactor 1D to the first reactor 1A is gradually decreased to shut off the supply of the reaction mixture to the first reactor 1A. Thereby, the first reactor 1A is placed in the non-operating state. Then, by the above-described switching mechanism 6, the supply amount of the peroxide to the fourth reactor 1D from the supply line 2 is gradually increased, and the supply amount of the peroxide to the second reactor 1B from the supply line 2 is gradually decreased to shut off the supply of the peroxide to the second reactor 1B from the supply line 2 as shown in FIG. 8.

Thereby, the titanosilicate in the first reactor 1A placed in the non-operating state is exchanged with one not deactivated while the epoxidation of propylene is performed (that is, the above-described epoxidation step is performed) in the fourth reactor 1D, the second reactor 1B, and the third reactor 1C.

<When Titanosilicate in Second Reactor 1B has been Deactivated>

Figures 9A, 9B:
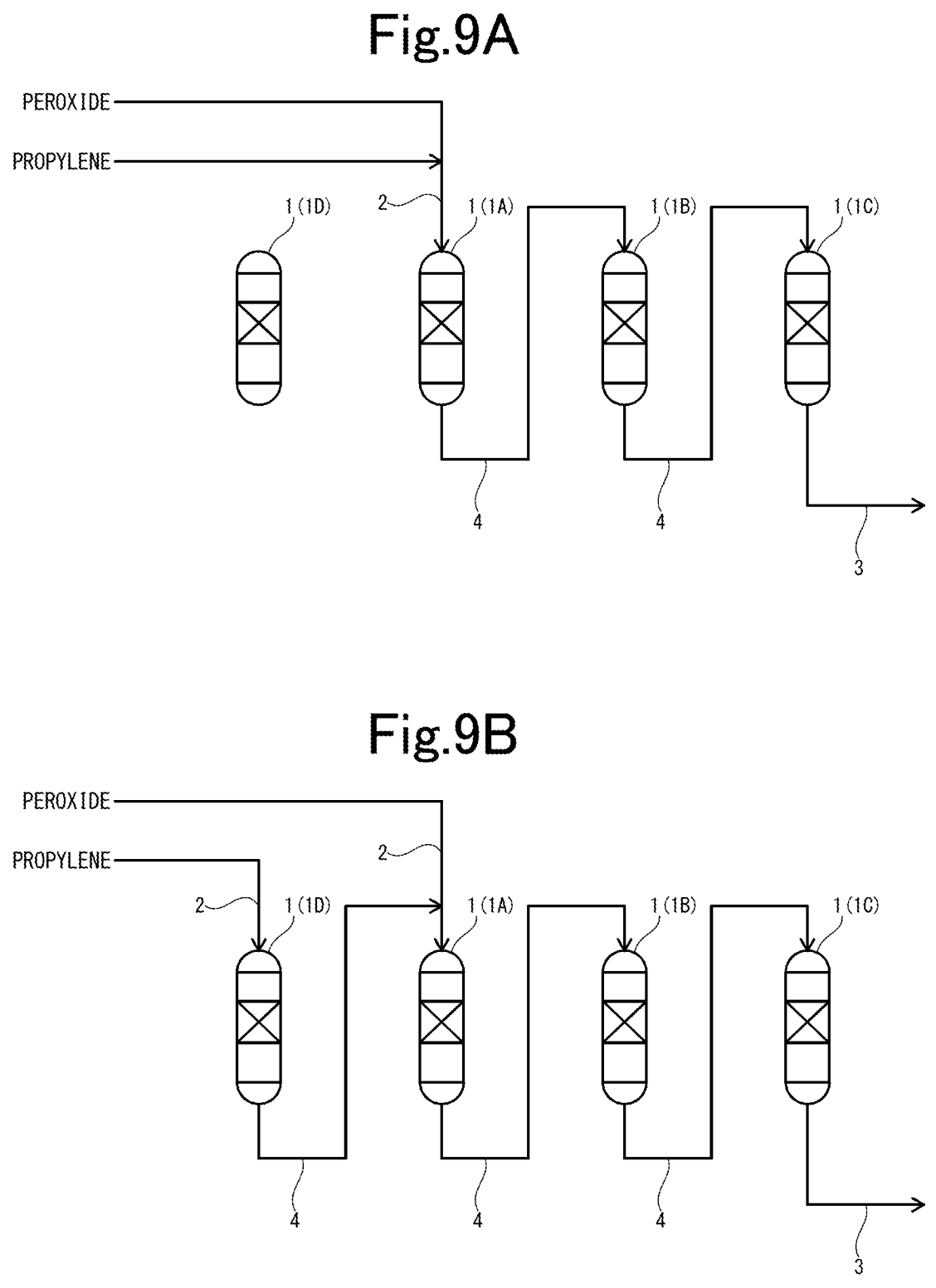

As shown in FIG. 9A, the first reactor 1A, the second reactor 1B, and the third reactor 1C are connected in series by the connection lines 4 and the epoxidation step is performed as described above with the fourth reactor 1D being in the non-operating state, and thereby when the titanosilicate in the second reactor 1B has been deactivated, switching is first performed gradually by the switching mechanism 6 in such a way that propylene which is being supplied to the first reactor 1A from the supply line 2 is supplied to the fourth reactor 1D, and switching is performed by the switching mechanism 6 in such a way that propylene which is discharged from the fourth reactor 1D is supplied to the first reactor 1A through the connection line 4, as shown in FIG. 9B. Thereby, propylene which is discharged from the fourth reactor 1D is supplied to the first reactor 1A.

The time for supplying propylene from the fourth reactor 1D to the first reactor 1A can be set in the same manner as described in <When Titanosilicate in Third Reactor 1C Has Been Deactivated>.

In addition, the temperature of the titanosilicate layer (the titanosilicate layer outlet temperature) during supplying propylene from the fourth reactor 1D to the first reactor 1A can be set in the same manner as described in <When Titanosilicate in Third Reactor 1C Has Been Deactivated>.

Furthermore, the ratio of the total flow volume (β) of propylene supplied until the peroxide is supplied to the volume (α) of the titanosilicate stored in the reactor 1 switched from the non-operating state to the operating state, (β/α), can be set in the same manner as described in <When Titanosilicate in Third Reactor 1C Has Been Deactivated>.

Figure 10A:
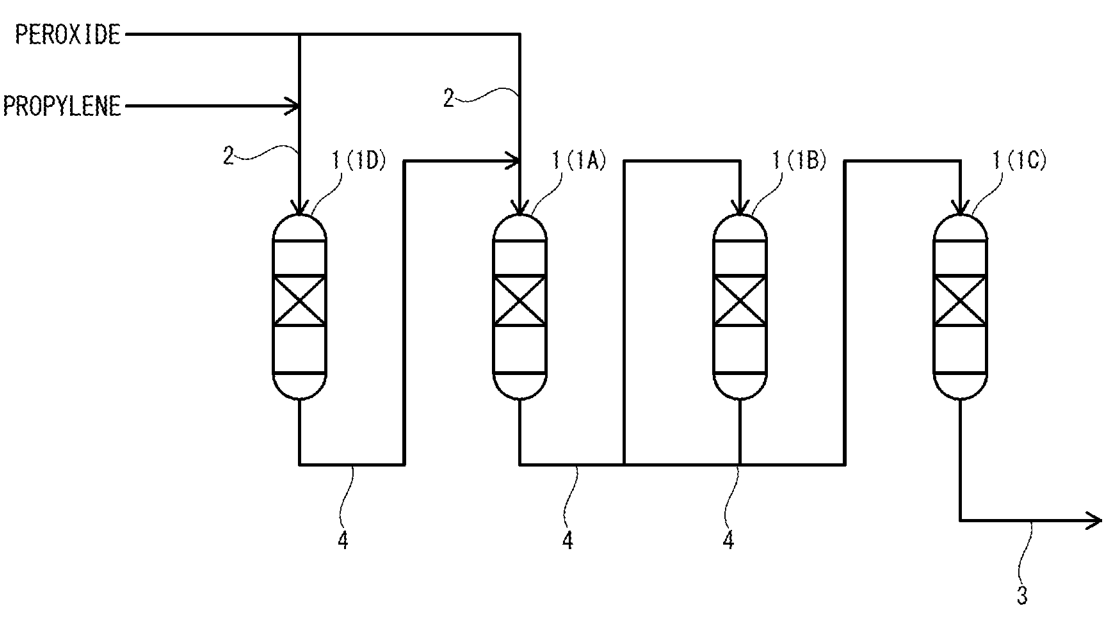
FIG. 10A is a schematic diagram showing a state after switching the connection state of reactors in the operating state from the state in FIG. 9B in the propylene oxide production apparatus of the same embodiment.

Next, as shown in FIG. 10A, switching is performed by the above-described switching mechanism 6 in such a way that part of the peroxide which has been supplied to the first reactor 1A from the supply line 2 is supplied to the fourth reactor 1D, and switching is performed by the above-described switching mechanism 6 in such a way that the reaction mixture which is discharged from the first reactor 1A is supplied to the third reactor 1C. Thereby, propylene is epoxidized in the fourth reactor 1D. Then, the reaction mixture which is discharged from the fourth reactor 1D is supplied to the first reactor 1A through the connection line 4, and the reaction mixture which is discharged from the first reactor 1A is supplied to the third reactor 1C through the connection line 4.

The temperature of the titanosilicate layer (the titanosilicate layer outlet temperature) after the peroxide is supplied to the fourth reactor 1D can be set in the same manner as described in <When Titanosilicate in Third Reactor 1C Has Been Deactivated>

Figure 10B:
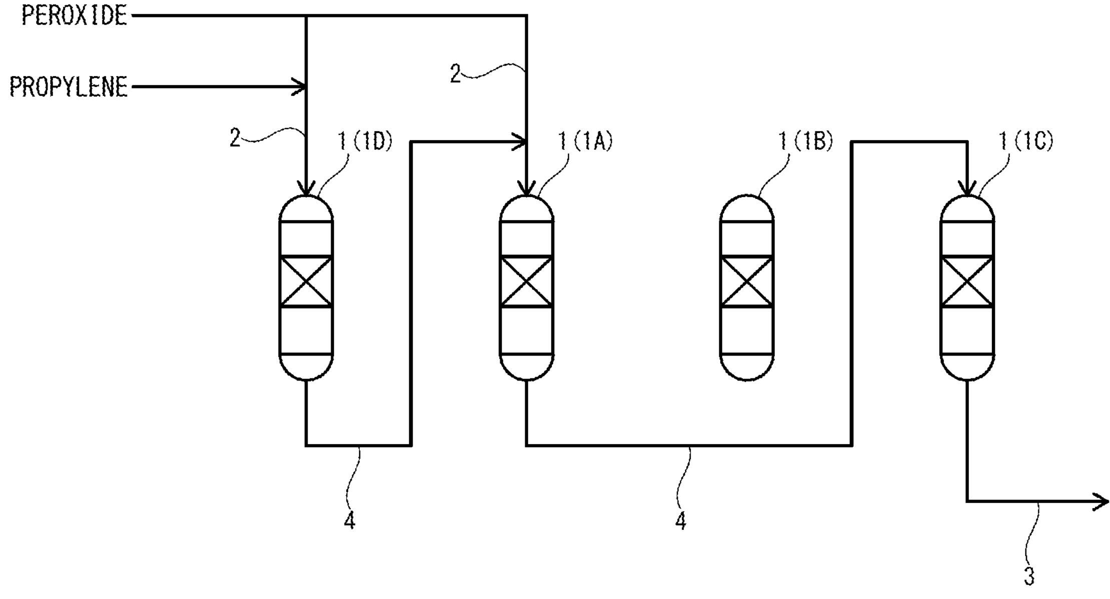
FIG. 10B is a schematic diagram showing a state after switching the connection state of reactors in the operating state from the state in FIG. 10A.

Next, by the above-described switching mechanism 6, the supply amount of the reaction mixture from the first reactor 1A to the third reactor 1C is gradually increased, the supply amount of the reaction mixture from the first reactor 1A to the second reactor 1B is gradually decreased, and further the supply amount of the reaction mixture from the second reactor 1B to the third reactor 1C is gradually decreased to shut off the supply of the reaction mixture to the second reactor 1B. Thereby, the second reactor 1B is placed in the non-operating state as shown in FIG. 10B.

Figure 11:
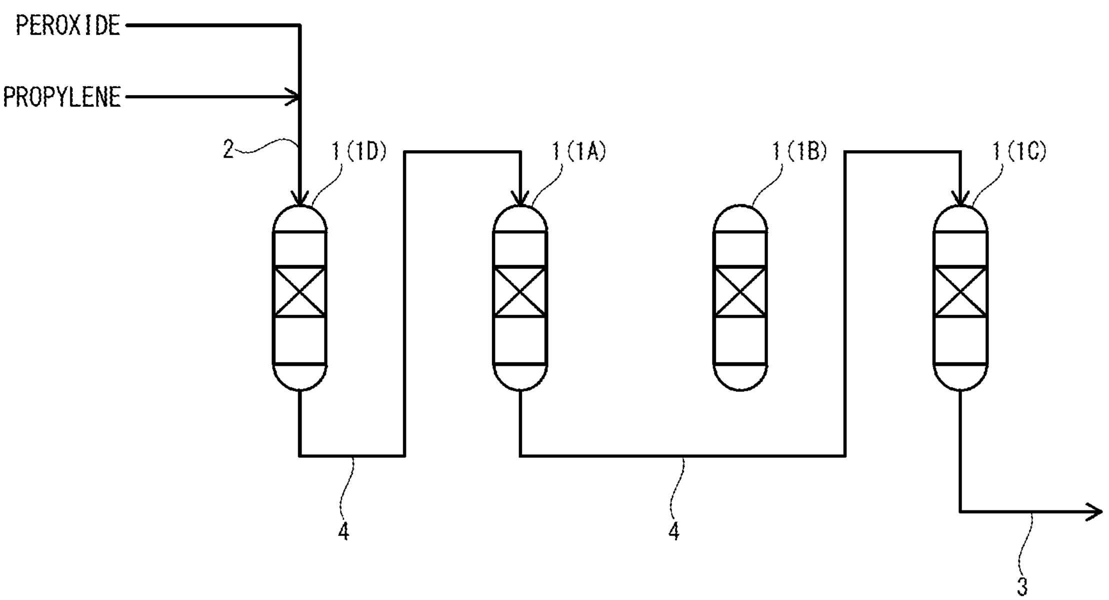
FIG. 11 is a schematic diagram showing a state after switching the connection state of reactors in the operating state from the state in FIG. 10B in the propylene oxide production apparatus of the same embodiment.

Then, by the above-described switching mechanism 6, the supply amount of the peroxide to the fourth reactor 1D from the supply line 2 is gradually increased, and the supply amount of the peroxide to the first reactor 1A from the supply line 2 is gradually decreased to shut off the supply of the peroxide to the first reactor 1A from the supply line 2 as shown in FIG. 11.

Thereby, the titanosilicate in the second reactor 1B placed in the non-operating state is exchanged with the titanosilicate not deactivated while the epoxidation of propylene is performed (that is, the above-described epoxidation step is performed) in the fourth reactor 1D, the first reactor 1A, and the third reactor 1C.

As described above, in exchanging the titanosilicate in each reactor 1, part of the reaction mixture in the discharge line 3 is sampled by the sampling mechanism 5 to check the deactivation status of the titanosilicate (sampling step) as shown in FIG. 1, and the reactor 1 in the operating state is switched to the non-operating state according to the deactivation status.

The deactivation status of the titanosilicate can be grasped based on the content (hereinafter, also referred to as "initial content") of a predetermined component in the reaction mixture which is discharged from the reactor 1 soon after being placed in the operating state and the content (hereinafter, also referred to as "content after use") of the predetermined component in the reaction mixture discharged from the reactor 1 used for a predetermined time after being placed in the operating state. For example, the deactivation status of the titanosilicate can be grasped by determining the activity k (specifically, the activity k0 based on the initial content and the activity ke based on the content after use) of the titanosilicate, which will be mentioned later.

In determining the initial content and the content after use, the sampling valve 5*b* of the sampling line 5*a* is opened to take part of the reaction mixture into the sampling line 5*a* from the discharge line 3. Subsequently, in a state where the reaction mixture has flown into the sealing part 5*c* of the sampling line 5*a*, two sealing valves 5*d*, 5*d* are closed to form a tightly closed region. Then, the reaction mixture is sampled from the sampling port of the sealing part 5*c* to determine the content (initial content or content after use) of a predetermined component in the sampled reaction mixture. The component whose content is to be determined is not particularly limited as long as it is a component having a relationship with the deactivation status of the titanosilicate, and examples thereof include the peroxide. In determining the content of the peroxide, a known method can be used, and iodometry or measurement with infrared rays (NIR) or by liquid chromatography (LC) can be used (however, when the measurement sample contains propylene, there is a need to correct the measurement result into a concentration excluding propylene).

The timing of switching the reactor 1 in the operating state to the non-operating state is preferably at the time when a ratio of the activity ke calculated from the content (the content after use) of the peroxide in the reaction mixture which is discharged from the reactor 1 in the operating state to the activity k0 calculated from the content (the initial content) of the peroxide in the reaction mixture sampled when the reactor 1 is switched to the operating state from the non-operating state, (ke/k0), becomes 1/2 to 1/50, more preferably ⅕ to 1/20. Note that the activity k (above-described k0 and above-described ke) of the titanosilicate is determined as follows.

The activation energy Ea (kJ/mol) of the titanosilicate is determined by forming an Arrhenius' plot for the titanosilicate to be used.

The contact time t is calculated using the following equation (1).

$$t(\text{time}) = (\text{volume of titanosilicate}) / \{(\text{mass of propylene supplied})/\rho C3' + (\text{mass of peroxide supplied})/\rho OX + (\text{mass of solvent for peroxide supplied})/\rho s\} \quad (1)$$

The "volume of titanosilicate" in the equation (1) is calculated by the following equation (2).

$$\text{Volume of titanosilicate}(L) = (\text{cross-sectional area of reactor 1 at position where titanosilicate layer } 1c \text{ is provided}) \times (\text{height of titanosilicate layer } 1c) \quad (2)$$

In the equation (1) and the following equations (3) and (4), "ρ" means density, and the density of the peroxide ρOX (g/ml)=0.985, density of the solvent diluting the peroxide ρs (g/ml)=0.886, and the density of propylene ρC3' (g/ml)=0.367 are used.

The molar concentration A of the peroxide and the molar concentration B of propylene are determined by the following equations (3) and (4).

$$\text{Molar concentration } A \text{ of peroxide (mol/L)} = \{(FOX) \times (\text{concentration of peroxide}) \times 1000\} / \{(FOX/\rho OX + Fs/\rho s + FC3'/\rho C3') \times (\text{molecular weight of peroxide})\} \quad (3)$$

$$\text{Molar concentration } B \text{ of propylene (mol/L)} = (FC3') \times 1000 / \{(FOX/\rho OX + Fs/\rho s + FC3'/\rho C3') \times (\text{molecular weight of propylene})\} \quad (4)$$

In the equations (3) and (4), "FOX" represents the mass (kg) of the peroxide supplied, "Fs" represents the mass (kg) of the solvent supplied, the solvent diluting the peroxide, and "FC3" represents the mass (kg) of propylene supplied.

The conversion X (%) of the peroxide is determined by the following equation (5).

$$\text{Conversion } X \text{ of peroxide (\%)} = \{(\text{peroxide concentration at reactor inlet}) - (\text{peroxide concentration at reactor outlet})\} / (\text{peroxide concentration at reactor inlet}) \times 100 \quad (5)$$

In the equation (5), the "reactor inlet" is the supply part 1*a*, and the "reactor outlet" is the discharge part 1*b*.

The "peroxide concentration at reactor inlet" can be obtained by sampling part of the reaction mixture from the supply part 1*a* to determine the content of the peroxide in the sampled reaction mixture, or can be obtained by determining the content of the peroxide in the reaction raw materials which are supplied from the supply line 2.

The "peroxide concentration at reactor outlet" can be obtained by sampling part of the reaction mixture from the sampling line 5*a* to determine the content of the peroxide in the sampled reaction mixture.

The average temperature Tav by trapezoidal integration is determined by the following equation (6).

$$\text{Average temperature } Tav \text{ by trapezoidal integration} = \{(T1 + T2) \times L2 + (T2 + T3) \times L3 + \ldots + (T(z-1) + Tz) \times Lz\} / 2 / (L2 + L3 + \cdots + Lz) \quad (6)$$

In the equation (6), "T1" represents the temperature of the supply part 1*a* of the reactor 1.

In the equation (6), "Tz" represents the temperature of the discharge part 1*b* of the reactor 1.

In the equation (6), "T2, T3 . . . . T(z−1)" represent temperatures that are measured at a plurality of temperature measurement parts provided at intervals in the height direction of the titanosilicate layer 1*c*, and the height of the temperature measurement part decreases in the mentioned order.

In the equation (6), "L2" represents the length between the uppermost part of the titanosilicate layer 1*c* and the temperature measuring part where the temperature is T2.

In the equation (6), "L3 . . . . L (z−1)" each represent the length between the temperature measurement parts adjacent to each other in the vertical direction in the temperature measurement parts corresponding to "T2, T3 . . . . T(z−1)" respectively.

In the equation (6), "Lz" represents the length between the lowermost part of the titanosilicate layer 1*c* and the temperature measuring part corresponding to T(z−1).

Then, the activity k is determined from the above-described "molar concentration A of peroxide," "molar concentration B of propylene," "contact time t," "conversion X of peroxide," "activation energy Ea of titanosilicate," and "average temperature Tav by trapezoidal integration" by the following equation (7).

$$\text{Activity } k = \left[1(B-A)\times\ln\{(B-AX/100)/(A-AX/100)\}\right]/t\times \exp\{-Ea\times 1000/8.13\times(Tav+273)/(80+273)\} \quad (7)$$

In switching the reactor 1 in the non-operating state in which titanosilicate has been exchanged to the operating state to start the supply of the raw materials, the reaction raw materials are preferably supplied in order of propylene and subsequently the peroxide. On this occasion, the ratio of the total flow volume (β) of propylene supplied in the reactor 1 switched from the non-operating state to the operating state until the peroxide is supplied to the volume (α) of the titanosilicate stored in the reactor 1 switched from the non-operating state to the operating state, (β/α), is preferably 5 to 6000, more preferably 600 to 3000. The volume of the titanosilicate can be determined from (cross-sectional area of reactor) x (height of titanosilicate layer 1*c*). The flow volume of propylene supplied can be calculated using the mass and density of propylene supplied.

Propylene which is supplied can contain an impurity such as propane or butane. The density generally changes depending on the impurity concentration, and the above-described flow volume of propylene is calculated assuming the density to be 0.5027 g/ml.

In addition, as described above, the titanosilicate layer outlet temperature in the reactor 1 during supplying only propylene to the reactor 1 switched to the operating state is preferably 40 to 150° C., more preferably 40 to 90.

Furthermore, as described above, the titanosilicate layer outlet temperature in the reactor 1 at the time of supplying the peroxide after supplying propylene to the reactor 1 switched to the operating state is preferably 40 to 150° C., more preferably 80 to 140° C.

The production apparatus 100 of the present embodiment is, as described above, a propylene oxide production apparatus that produces propylene oxide by epoxidizing propylene using a peroxide in the presence of a titanosilicate, the apparatus including: at least three reactors 1 in which the titanosilicate is stored and to which propylene and the peroxide are supplied as reaction raw materials; a supply line that supplies the reaction raw materials, which have not yet supplied to each reactor, to each reactor; a discharge line 3 that is connected to each reactor 1 and that discharges a reaction mixture containing propylene oxide from each reactor 1; a switching mechanism 6 that is capable of switching a state of each reactor 1 between an operating state where the reaction raw materials are supplied and an epoxidation reaction is performed and a non-operating state where the supply of the reaction raw materials is shut off, that is capable of changing a reactor 1 in the non-operating state one by one, and that performs switching in such a way that only reactors 1 in the operating state are connected fluidically in series or in parallel, thereby enabling supplying the reaction raw materials to the reactors 1 in the operating state; and a sampling mechanism 5 that samples part of the reaction mixture from each discharge line 3 that is connected to each reactor 1.

According to such a configuration, the reactor 1 in the non-operating state is changed one by one and the titanosilicate can be exchanged while the epoxidation of propylene is performed in the reactors 1 in the operating state. Thereby, the titanosilicate can be exchanged while the generation of propylene oxide is performed, and therefore propylene oxide can efficiently be produced.

In addition, since the production apparatus includes the sampling mechanism 5, components in each reaction mixture which is discharged from each reactor 1 can be grasped. Thereby, lowering of the activity of the titanosilicate (deactivation status) can be grasped, and therefore the timing of exchanging the titanosilicate can easily be determined for every reactor 1.

Further, the production apparatus 100 of the present embodiment includes a connection line 4 that connects the reactors 1 fluidically with each other and supplies the reaction mixture which is discharged from one of the connected reactors 1 and which contains the reaction raw materials to another reactor 1, and the switching mechanism 6 connects only the reactors 1 in the operating state in series by the connection line or lines 4.

According to such a configuration, only the reactors 1 in the operating state can be connected in series by the connection line 4. Thereby, the reaction raw materials are supplied to the reactors 1 in the operating state and thereby flow in a plurality of reactors 1, and therefore the generation of propylene oxide can efficiently be performed.

In addition, each reactor 1 includes: a supply part 1*a* to which the reaction raw materials are supplied; and a discharge part 1*b* from which the reaction mixture is discharged, and the production apparatus 100 includes thermometers that measure the internal temperatures of the supply part 1*a* and the discharge part 1*b* respectively.

Here, the epoxidation reaction between the peroxide and propylene is an exothermic reaction. Therefore, the temperature difference between the discharge part 1*b* and the supply part 1*a* becoming smaller indicates lowering of the activity of the titanosilicate. Therefore, lowering of the activity of the titanosilicate can be grasped by the temperatures measured with the thermometers.

Further, each reactor 1 includes a titanosilicate layer 1*c* formed by the stored titanosilicate, and the production apparatus 100 includes a thermometer that measures the internal temperature of the titanosilicate layer 1*c*.

As described above, the epoxidation reaction between the peroxide and propylene is an exothermic reaction. Therefore, the temperature difference between the discharge part 1*b* and the supply part 1*a* becoming smaller indicates lowering of the activity of the titanosilicate. Therefore, lowering of the activity of the titanosilicate can be grasped by the temperature measured with the thermometer.

Further, each reactor 1 includes: a supply part 1*a* to which the reaction raw materials are supplied; and a discharge part 1*b* that discharges the reaction mixture, and the production apparatus 100 includes pressure gauges that measure the internal pressures of the supply part 1*a* and the discharge part 1*b* respectively.

According to such a configuration, variations in the pressure loss of the titanosilicate can be grasped by the pressures measured with the pressure gauges. By grasping an increase in the pressure loss due to powdering of the catalyst, a clogged material, or the like using the pressure gauges, failure of equipment such as a pump which is used for supplying the reaction raw materials can be prevented. The timing of switching the reactor in the case where the lowering of the activity of the titanosilicate is not a cause of switching can easily be grasped by the pressure gauges.

Further, in the production apparatus 100 of the present embodiment, at least three of the reactors 1 have approximately the same size.

The production apparatus 100 is operated while switching the reactor 1 in the non-operating state and the reactor 1 in the operating state, and therefore when the sizes of the reactors 1 are different, adjustment of the retention time and the temperature is complicated, so that it is difficult to control the operation, but when the sizes of the reactors 1 are approximately the same, controllability of operation can be improved. In addition, each reactor 1 has a cylindrical shape, and when the inner diameter of the reactor 1 is assumed to be D (m) and the height of the reactor 1 is assumed to be L (m), L/D is 0.5 to 20.

According to such a configuration, since L/D is in the above-described ranges, a deviated flow of the fluid in the titanosilicate layer is suppressed, and therefore lowering of the efficiency of generating propylene oxide due to the deviated flow can be suppressed.

Further, each reactor 1 includes a pressure release valve capable of releasing the internal pressure.

According to such a configuration, since each reactor 1 includes a pressure release valve, the pressure in the reactor 1 can be released outside the reactor 1 even if the pressure in the reactor 1 increases up to an unintended pressure. Thereby, breakage of the reactor 1 or lowering of the efficiency of generating propylene oxide, caused by the internal pressure of the reactor 1 can be prevented.

In addition, the sampling mechanism 5 includes a sampling line 5*a* that branches from each discharge lines 3 that is connected to each reactor 1 and that takes in part of the reaction mixture, and the inner diameter of the sampling line 5*a* is smaller than the inner diameter of the discharge line 3 to which the sampling line 5*a* is connected.

According to such a configuration, since the inner diameter of the sampling line 5*a* is smaller than the inner diameter of the discharge line 3 to which the sampling line 5*a* is connected, the flow amount of the reaction mixture flowing in the sampling line 5*a* is smaller than the flow amount of the reaction mixture flowing in the discharge line 3, and therefore sampling can be performed more safely than sampling of the reaction mixture from the discharge line 3.

Further, the sampling line 5*a* includes a sealing part 5*c* capable of forming a tightly closed region to retain the reaction mixture and has a sampling port at the sealing part 5*c*.

According to such a configuration, since the sampling port is provided at the sealing part 5*c* included in the sampling line Sa, the reaction mixture retained in the sealing part 5*c* can be sampled. Therefore, sampling can be performed more safely than sampling from the reaction mixture flowing in the sampling line 5*a*.

Further, the titanosilicate is preferably a silylated titanosilicate.

According to such a configuration, the titanosilicate surface is made hydrophobic by the silylation, and therefore propylene that is the reaction raw material easily diffuses in the titanosilicate, so that the reaction rate is improved.

Further, the titanosilicate is preferably a titanosilicate silylated with 1,1,1,3,3,3-hexamethyldisilazane.

1,1,1,3,3,3-Hexamethyldisilazane is a silylating agent that is relatively inexpensive and easy to handle, and therefore the silylated titanosilicate can be obtained relatively inexpensively and easily.

Further, the peroxide can be an organic peroxide.

Further, the organic peroxide can be at least one selected from the group consisting of cumene hydroperoxide, ethylbenzene hydroperoxide, and tert-butyl hydroperoxide.

A propylene oxide production method of the present embodiment is a propylene oxide production method using the propylene oxide production apparatus described above and repeating (1) a first step of exchanging the titanosilicate in the reactor 1 in the non-operating state while supplying the reaction raw materials to the reactors 1 in the operating state and performing the epoxidation, and (2) a second step of switching the reactor 1 in the non-operating state, in which the titanosilicate has been exchanged, to the operating state and switching one or some reactors 1 of a plurality of the reactors 1 in the operating state to the non-operating state by the switching mechanism 6, and supplying the reaction raw materials to the reactors 1 in the operating state and performing the epoxidation, thereby performing the epoxidation while changing the reactor 1 to be placed in the non-operating state one by one to exchange the titanosilicate, and the method further includes (3) a sampling step of sampling part of the reaction mixture by the sampling mechanism 5 and checking a deactivation status of the titanosilicate.

According to such a configuration, by performing the above-described first step and second step, the reactor 1 in the non-operating state is changed one by one and the titanosilicate can be exchanged while the epoxidation of propylene in the reactors 1 in the operating state is performed. Thereby, the titanosilicate can be exchanged while the generation of propylene oxide is performed, and therefore propylene oxide can efficiently be produced.

In addition, since the production method includes the sampling step, components in each reaction mixture which is discharged from each reactor 1 can be grasped. Thereby, lowering of the activity of the titanosilicate (deactivation status) can be grasped, and therefore the timing of exchanging the titanosilicate can easily be determined for every reactor 1.

A propylene oxide production method of the present embodiment is a propylene oxide production method using the propylene oxide production apparatus described above and repeating (1) a first step of exchanging the titanosilicate in the reactor 1 in the non-operating state while connecting only the reactors 1 in the operating state in series by the connection line or lines 4 and supplying the reaction raw materials to the reactors 1 in the operating state and performing the epoxidation, and (2) a second step of switching the reactor 1 in the non-operating state in which the titanosilicate has been exchanged to the operating state, switching one or some reactors 1 of a plurality of the reactors 1 in the operating state to the non-operating state, connecting only the reactors 1 in the operating state in series by the connection line or lines 4, and supplying the reaction raw materials to the reactors 1 in the operating state by the switching mechanism 6 and performing the epoxidation, thereby performing the epoxidation while changing the reactor 1 to be placed in the non-operating state one by one to exchange the titanosilicate, and the method further includes (3) a sampling step of sampling part of the reaction mixture by the sampling mechanism 5 and checking a deactivation status of the titanosilicate.

According to such a configuration, since the production method includes the first step and the second step, at least two reactors 1 in the operating state are connected in series by the connection line 4, the reaction raw materials are supplied to at least one reactor 1 in the operating state from the supply line 2, and the reaction raw materials are supplied to at least one reactor 1 in the operating state from the connection line 4, thereby propylene that is the reaction raw material passes through a plurality of reactors 1 and is epoxidized, and therefore the generation of propylene oxide can efficiently be performed.

In addition, since the production method includes the sampling step, components in each reaction mixture which is discharged from each reactor 1 can be grasped. Thereby, lowering of the activity of the titanosilicate (deactivation status) can be grasped, and therefore the timing of exchanging the titanosilicate can easily be determined for every reactor 1.

In the propylene oxide production method of the present embodiment, the timing of switching one or some of the reactors 1 to the non-operating state in the second step is preferably determined according to the deactivation status of the titanosilicate.

According to such a configuration, by determining the timing of switching one or some of the reactors 1 to the non-operating state in the second step according to the deactivation status of the titanosilicate checked in the sampling step, the timing of exchanging the titanosilicate can easily be determined for every reactor 1.

The propylene oxide production method of the present embodiment can include a step of separating an alcohol from the reaction mixture.

In the propylene oxide production method of the present embodiment, the second step includes a first supply step of switching the reactor 1 in the non-operating state, in which titanosilicate has been exchanged, to the operating state and supplying the reaction raw materials in order of propylene and subsequently the peroxide, and in the first supply step, a ratio of a total flow volume (β) of propylene supplied until the peroxide is supplied in the reactor 1 switched from the non-operating state to the operating state to a volume (α) of the titanosilicate stored in the reactor 1 switched from the non-operating state to the operating state, (β/α), is preferably set to 5 to 6000, more preferably 600 to 3000.

According to such a configuration, in the alcohol-converting step of converting the alcohol, obtained by separation from the reaction mixture obtained through the epoxidation step, into another compound, the conversion of the alcohol can be increased.

In the propylene oxide production method of the present embodiment, the titanosilicate layer outlet temperature in the reactor 1 in supplying the peroxide to the reactors 1 and switching the reactor 1 in the non-operating state to the operating state in the first supply step is preferably set to 40 to 150° C.

According to such a configuration, the titanosilicate layer outlet temperature is preferably 40° C. or higher from the viewpoint of allowing the epoxidation reaction to progress efficiently. The titanosilicate layer outlet temperature is preferably 150° C. or lower from the viewpoint of suppressing generation of by-product in the epoxidation reaction. Examples of the by-product include substances generated by decomposition of the peroxide and substances obtained by conversion of propylene oxide that is the product.

In the propylene oxide production method of the present embodiment, the titanosilicate outlet temperature in the reactor 1 is preferably set to 40 to 150° C. during supplying only propylene to the reactor 1 in the first supply step.

According to such a configuration, vaporization of propylene in the reactor 1 can be prevented, and heat efficiency can be improved.

Note that the propylene oxide production apparatus and the propylene oxide production method of the present invention are not limited to the above-described embodiment, various modifications can be made in the range without deviating from the gist of the present invention. In addition, the configurations, the methods, and the like other than those described above can be arbitrarily adopted and combined, and the configuration, the method, and the like of one embodiment described above can be applied to the configurations, methods, and the like of the other embodiments.

Figure 12A:
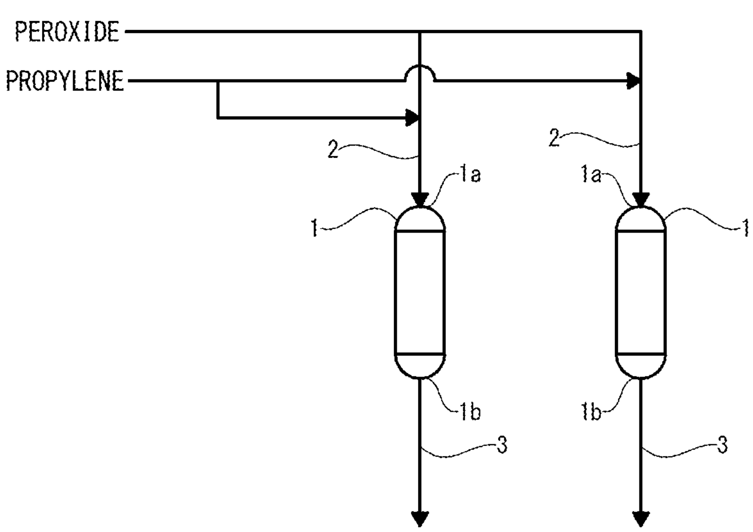
FIG. 12A is a schematic diagram showing the connection state of reactors in the operating state in a propylene oxide production apparatus of another embodiment.
Figure 12B:
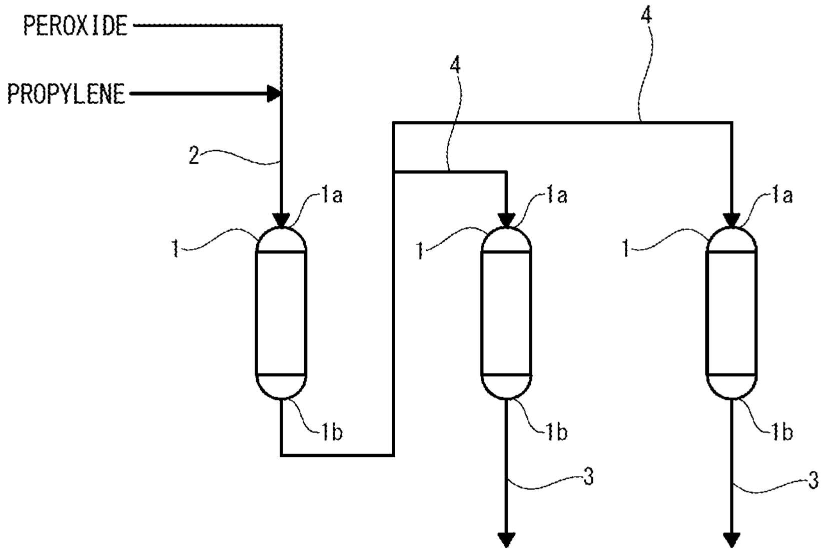
FIG. 12B is a schematic diagram showing the connection state of reactors in the operating state in a propylene oxide production apparatus of yet another embodiment.
Figure 13A:
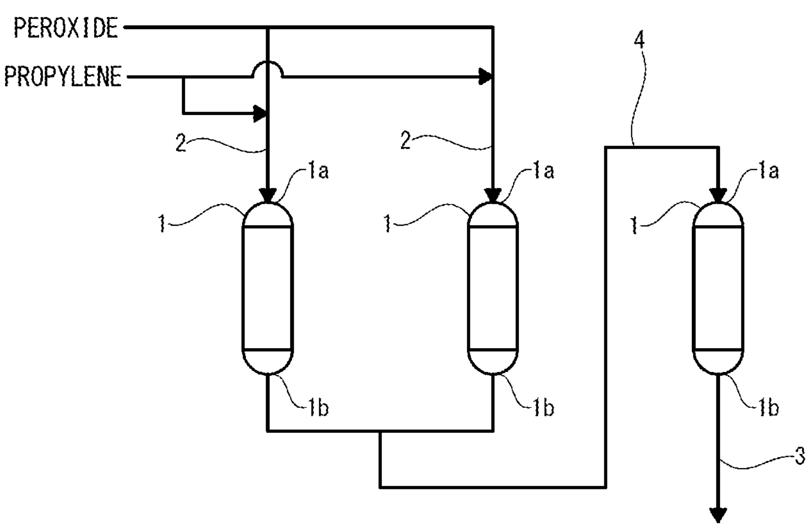
FIG. 13A is a schematic diagram showing the connection state of reactors in the operating state in a propylene oxide production apparatus of still yet another embodiment.
Figure 13B:
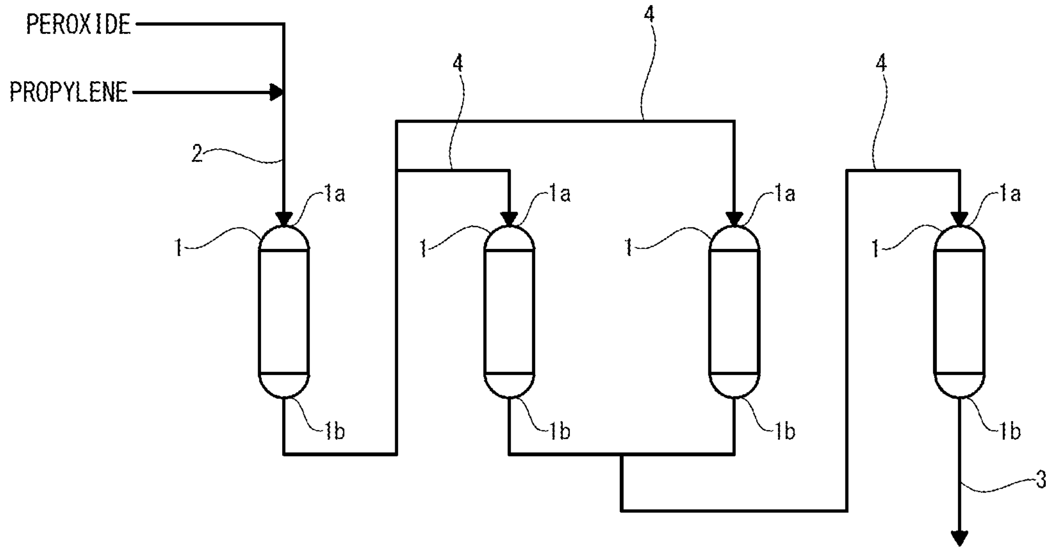
FIG. 13B is a schematic diagram showing the connection state of reactors in the operating state in a propylene oxide production apparatus of further another embodiment.

For example, in the above-described embodiment, all of the reactors 1 in the operating state are configured in such a way as to be connected in series by the connection line or lines 4 and perform the epoxidation step, but the present invention is not limited to this, and, for example, as shown in FIG. 12A, all of the reactors 1 in the operating state can be configured in such a way as to be connected in parallel (in other words, in a connection state in which the reaction mixture is not suppled from one reactor 1 to another reactor 1).

Further, in the above-described embodiment, all of a plurality of the reactors in the operating state are configured in such a way as to be connected in series by the connection line or lines 4 and perform the epoxidation step, but the present invention is not limited to this, and, for example, as shown in FIG. 12B to FIG. 13B, a plurality of the reactors in the operating state can be configured in such a way that parts where the reactors 1 are connected in series by the connection line or lines 4 and a part where the reactors 1 are connected in parallel by the connection line or lines 4 are mixed.

Further, in the above-described embodiment, all of the reactors 1 are configured in such a way as to have approximately the same size, but the present invention is not limited to this, and, for example, all of the reactors 1 can be configured in such a way that all of the reactors 1 each have a different size.

Further, in the above-described embodiment, the supply of the reaction raw materials to each reactor 1 is performed by one of the supply line 2 and the connection line 4 in the epoxidation step, but the present invention is not limited to this, and, for example, the supply of the reaction raw materials to the reactor 1 can be performed from both of the supply line 2 and the connection line 4.

Further, in the above-described embodiment, the sampling port is provided at the sampling line 5*a* branching from the discharge line 3, but the present invention is not limited to this, and, for example, a configuration can be made in such a way that the sampling port is provided at the discharge line 3 itself to sample the reaction mixture directly from the discharge line 3.

Further, in the above-described embodiment, a particular reactor 1 is configured in such a way as to be the foremost reactor 1 among a plurality of reactors 1 connected in series, but the present invention is not limited to this, and, for example, any reactor of a plurality of reactors 1 can be set to be the foremost reactor 1 among a plurality of the reactors 1 connected in series in the production apparatus 100.

EXAMPLES

Hereinafter, the present invention will more specifically be described by

Operation Examples and Test Examples, but the present invention is not limited to the following Operation Examples and Test Examples.

[Test 1]

1. Facilities and Materials Used

Reactors 1: five reactors 1 in the above-described embodiment were used.

Solution of peroxide: cumene (CUM) solution containing cumene hydroperoxide (CMHP).

Propylene solution

2. Operation Example 1

Figures 14A, 14B, 14C:
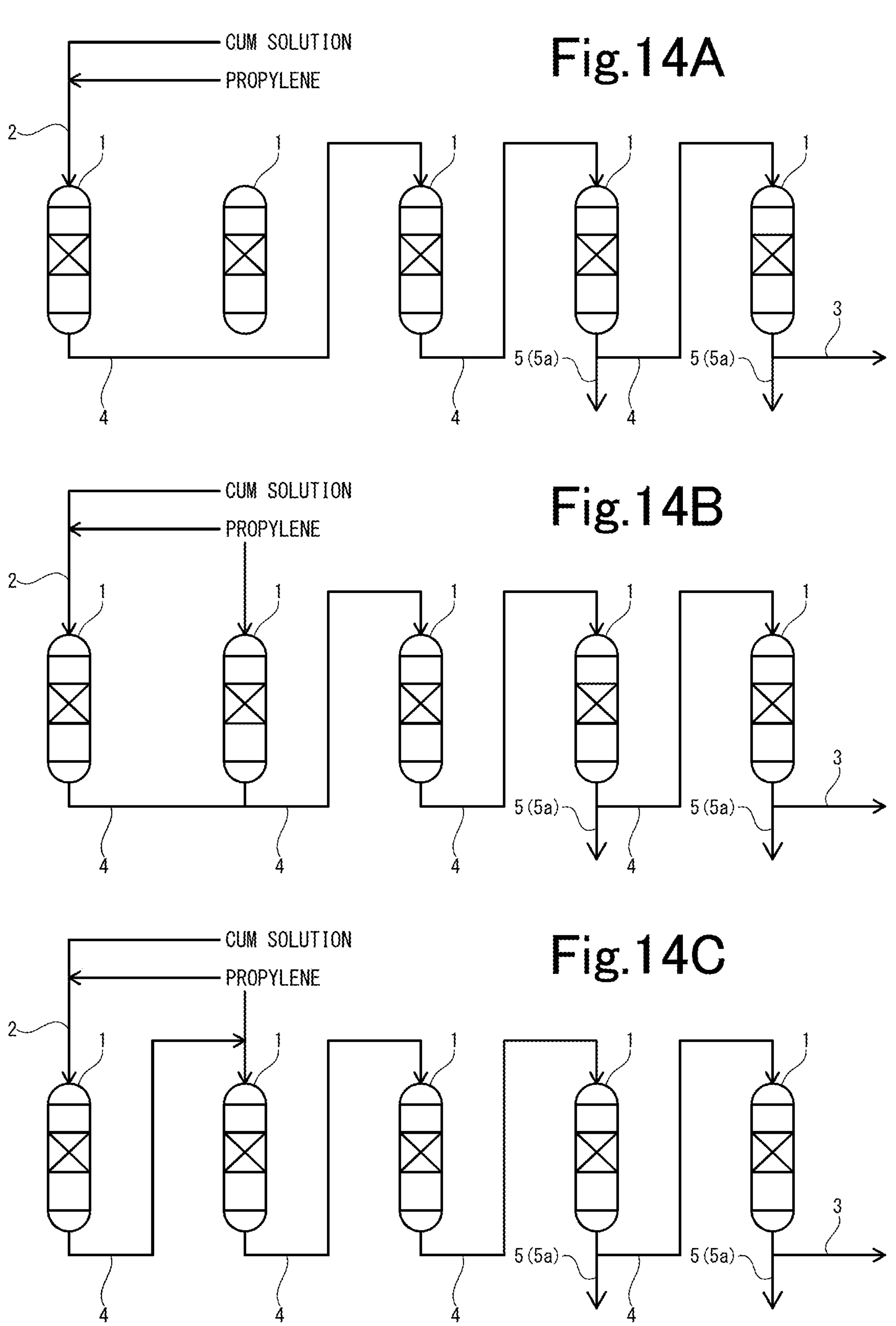
FIG. 14A is a schematic diagram showing the connection state of reactors in the operating state for Operation Example 1 of Test 1 in Examples.
FIG. 14B is a schematic diagram showing a state after switching the connection state of reactors in the operating state from the state in FIG. 14A.
FIG. 14C is a schematic diagram showing a state after switching the connection state of reactors in the operating state from the state in FIG. 14B.
Figures 15A, 15B, 15C:
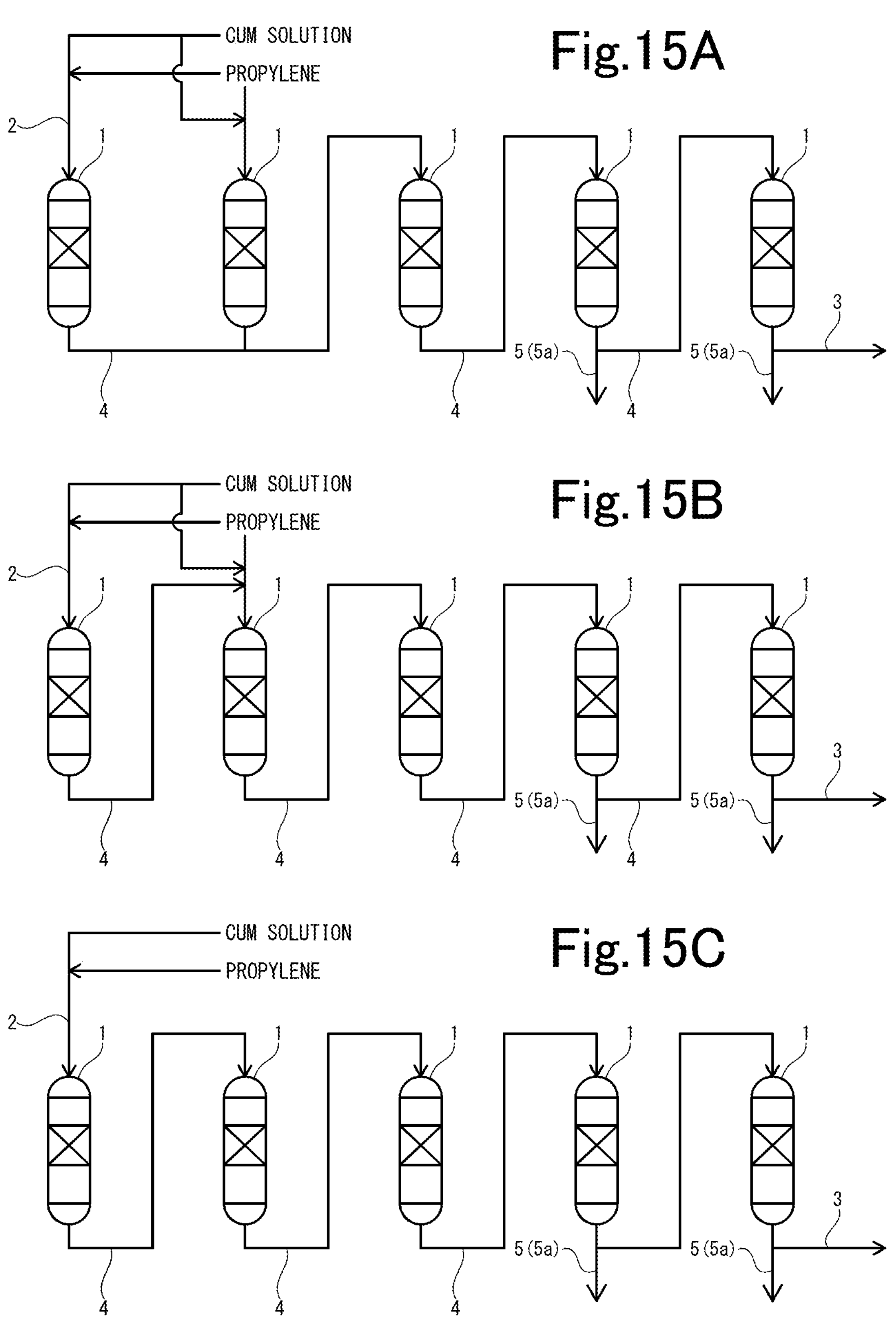
FIG. 15A is a schematic diagram showing a state after switching the connection state of reactors in the operating state from the state in FIG. 14C for Operation Example 1 of Test 1 in Examples.
FIG. 15B is a schematic diagram showing a state after switching the connection state of reactors in the operating state from the state in FIG. 15A.
FIG. 15C is a schematic diagram showing a state after switching the connection state of reactors in the operating state from the state in FIG. 15B.
Figure 16:
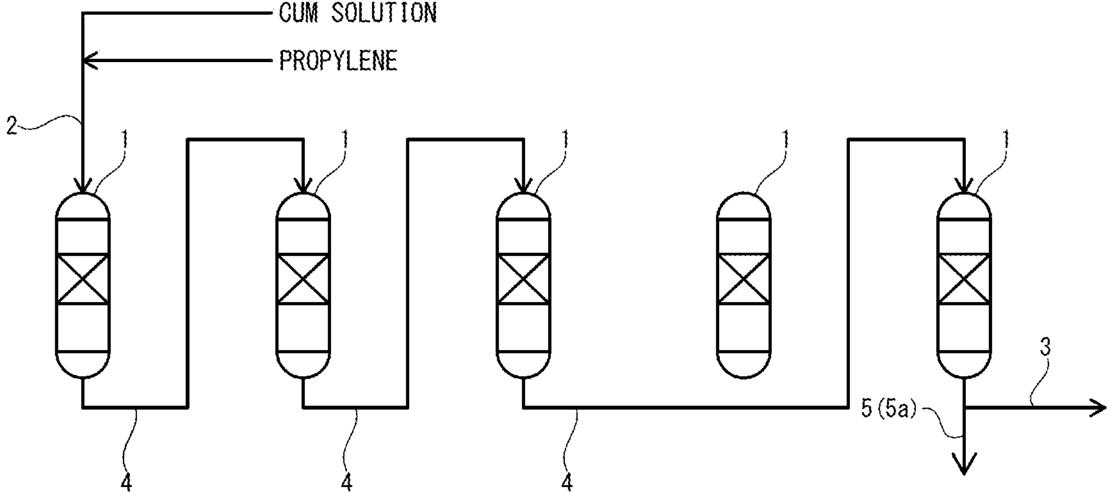
FIG. 16 is a schematic diagram showing a state after switching the connection state of reactors in the operating state from the state in FIG. 15C for Operation Example 1 of Test 1 in Examples.

In Operation Example 1, the connection states between the reactors 1 were switched in order of four-reactor operation shown in FIG. 14A, five-reactor operation shown in FIG. 15C, and four-reactor operation shown in FIG. 16. Specifically, the connection states were as follows.

<Four-Reactor Operation>

As shown in FIG. 14A, one of the five reactors 1 was placed in the non-operating state, and four reactors 1 were placed in the operating state and connected in series by the connection lines 4. Then, the CUM solution and the propylene solution were then supplied to the first or foremost reactor 1 and the epoxidation step was performed as in the above-described embodiment, and thereby propylene oxide (PO) was produced.

In addition, the reaction mixture was sampled from the sampling lines 5*a* that branch from the discharge lines 3 which are connected to the reactors 1 corresponding to the third reactor 1 and the fourth reactor 1 of the reactors 1 connected in series and that take in part of the reaction mixture.

Note that the ratio of (outer diameter of discharge line 3)/(outer diameter of sampling line 5*a*) was set to 13.

The conversion of CMHP in the third reactor 1, based on CMHP supplied to the first reactor 1, was 98.1%. In addition, the conversion of CMHP in the fourth reactor 1, based on CMHP supplied to the first reactor 1, was 99.3%. Note that the conversion of CMHP was calculated from the following equation (9).

$$\text{Conversion of } CMHP(\%) = \{(CMHP \text{ concentration in } CUM \text{ solution supplied to first reactor 1}) - (CMHP \text{ concentration in reaction mixture discharged from the } n\text{-th reactor 1})\} / (CMHP \text{ concentration in } CUM \text{ solution supplied to first reactor 1}) \times 100 \quad (9)$$

* n means the number of reactors subjected to sampling.

<Five-Reactor Operation>

As shown in FIG. 14B, only the propylene solution was supplied to the reactor 1 in the non-operating state, and thereafter, as shown in FIG. 14C, the reaction mixture was supplied from the first reactor 1 to the reactor 1 in the non-operating state while the supply of the propylene solution was maintained, and thus the reactor 1 in the non-operating state was used as the second reactor 1 in the operating state.

Thereafter, as shown in FIG. 15A, the supply of the reaction mixture from the first reactor 1 to the second reactor 1 was stopped and the CUM solution was supplied to the second reactor 1 while the supply of the propylene solution to the second reactor 1 was maintained.

Then, as shown in FIG. 15B, the reaction mixture was supplied from the first reactor 1 to the second reactor 1 while the supply of the propylene solution and the CUM solution to the second reactor 1 was maintained.

Thereafter, as shown in FIG. 15C, the supply of the propylene solution and the CUM solution to the second reactor 1 was stopped while the supply of the reaction mixture from the first reactor 1 to the second reactor 1 was maintained, so that five reactors 1 in the operating state were placed in a state of being connected in series by the connection lines 4, and thereby the epoxidation step was performed and propylene oxide (PO) was produced as in the above-described embodiment.

In addition, the reaction mixture was sampled from the sampling lines 5*a* that branch from the discharge lines 3 connected to the reactors 1 corresponding to the fourth reactor 1 and the fifth reactor 1 of the reactors 1 connected in series and that take in part of the reaction mixture.

The conversion of CMHP in the fourth reactor 1, based on CMHP supplied to the first reactor 1, was 99.9%. In addition, the conversion of CMHP in the fifth reactor 1, based on CMHP supplied to the first reactor 1, was 100.0% (see Table 1 below).

<Four-Reactor Operation>

As shown in FIG. 16, the reactor 1 corresponding to the fourth reactor 1 of the five reactors 1 under operation was cut off from the other reactors 1 to switch the reactor 1 to the non-operating state, and switching was performed in such a way that the reaction mixture discharged from the third reactor 1 was supplied to the fifth reactor 1, and thus the fifth reactor 1 was used as the fourth reactor 1. Then, the CUM solution and the propylene solution were supplied to the first reactor 1 and the epoxidation step was performed as in the above-described embodiment, and thereby propylene oxide (PO) was produced.

In addition, the reaction mixture was sampled from the sampling line 5*a* that branches from the discharge line 3 connected to the reactor 1 corresponding to the fourth reactor 1 of the reactors 1 connected in series and that takes in part of the reaction mixture.

The conversion of CMHP in the fourth reactor 1, based on CMHP supplied to the first reactor 1, was 99.9%.

3. Operation Example 2

Figures 17A, 17B, 17C:
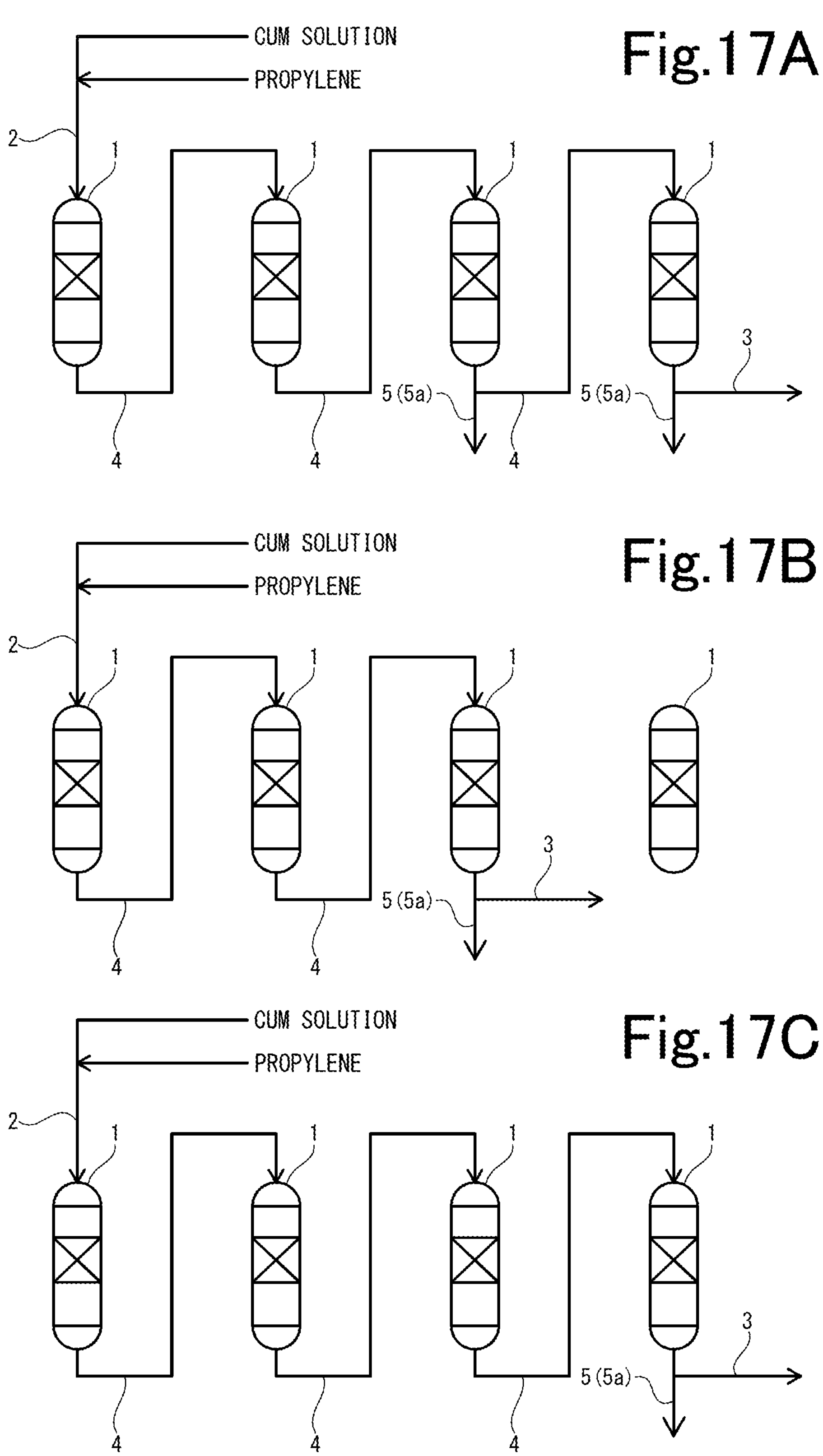
FIG. 17A is a schematic diagram showing the connection state of reactors in the operating state for Operation Example 2 of Test 1 in Examples.
FIG. 17B is a schematic diagram showing a state after switching the connection state of reactors in the operating state from the state in FIG. 17A.
FIG. 17C is a schematic diagram showing a state after switching the connection state of reactors in the operating state from the state in FIG. 17B.

In Operation Example 2, the connection states between the reactors 1 were switched in order of four-reactor operation shown in FIG. 17A, three-reactor operation shown in FIG. 17B, and four-reactor operation shown in FIG. 17C. Specifically, the connection states were as follows.

<Four-Reactor Operation>

As shown in FIG. 17A, the four reactors 1 in the operating state were connected in series by the connection lines 4. Then, the CUM solution and the propylene solution were supplied to the first reactor 1 and the epoxidation step was performed as in the above-described embodiment, and thereby propylene oxide (PO) was produced.

In addition, the reaction mixture was sampled from the sampling lines 5*a* that branch from the discharge lines 3 connected to the reactors 1 corresponding to the third reactor 1 and the fourth reactor 1 of the reactors 1 connected in series and that take in part of the reaction mixture.

Note that the ratio of (outer diameter of discharge line 3)/(outer diameter of sampling line 5*a*) was 13.

The conversion of CMHP in the third reactor 1, based on CMHP supplied to the first reactor 1, was 98.1%. In addition, the conversion of CMHP in the fourth reactor 1, based on CMHP supplied to the first reactor 1, was 99.3%.

<Three-Reactor Operation>

The reactor 1 corresponding to the fourth reactor 1 of the four reactors under operation was cut off from the other reactors 1 to switch the fourth reactor 1 to the non-operating state as shown in FIG. 17B. Then, the CUM solution and the propylene solution were supplied to the first reactor 1 and the epoxidation step was performed as in the above-described embodiment, and thereby propylene oxide (PO) was produced.

In addition, the reaction mixture was sampled from the sampling line 5*a* that branches from the discharge line 3 connected to the reactor 1 corresponding to the third reactor 1 of the reactors 1 connected in series and that takes in part of the reaction mixture.

The conversion of CMHP in the fourth reactor 1, based on CMHP supplied to the first reactor 1, was 98.1% (see Table 1 below).

<Four-Reactor Operation>

As shown in FIG. 17C, the reactor 1 in the non-operating state was switched to the operating state, and the four reactors 1 in the operating state were connected in series by the connection lines 4 in such a way that the reactor 1 in the non-operating state switched to the operating state was used as the fourth reactor 1. Then, the CUM solution and the propylene solution were supplied to the first reactor 1 and the epoxidation step was performed as in the above-described embodiment, and thereby propylene oxide (PO) was produced.

In addition, the reaction mixture was sampled from the sampling line 5*a* that branches from the discharge line 3 connected to the reactor 1 corresponding to the fourth reactor 1 of the reactors 1 connected in series and that takes in part of the reaction mixture.

The conversion of CMHP in the fourth reactor 1, based on CMHP supplied to the first reactor 1, was 99.9%.

TABLE 1

| | Conversion of CMHP |
|---|---|
| Operation Example 1 (during five-reactor operation) | 100% |
| Operation Example 2 (during three-reactor operation) | 98% |

[Test 2]

<Conversion of Cumyl Alcohol (CMA) and Conversion of α-Methylstyrene (AMS)>

Test Example 1

1. Epoxidation Reaction Step

A metal reactor (the metal reactor includes a sheath tube having an outer diameter of 6 mm, the sheath tube including a thermometer therein) having an inner diameter of 16 mm was filled with a catalyst (3.5 g or 10 ml of a titanosilicate prepared in accordance with Example 1 in JP 2004-195379 A). The catalyst was held as a fixed bed having a filling length of 6 cm.

Propylene was supplied at 0.8 g/min simultaneously with the start of heating the reactor in an electric furnace. The pressure in the reactor was increased by the supply of propylene, and PCV (flow valve) at the outlet was adjusted in such a way that the pressure became 6 MPa-G. The catalyst layer outlet temperature reached 120° C. 60 minutes later. Thereafter, the electric furnace temperature was adjusted in such a way that the catalyst layer outlet temperature was 120° C., and propylene was supplied for 406 minutes in total. The ratio of volume of propylene supplied at that time/volume of titanosilicate was 64.6.

Thereafter, 3 wt % CMHP/CUM/CMA was supplied at 2.25 g/min. The catalyst layer outlet temperature 60 minutes after the start of the supply of 3 wt % CMHP/CUM/CMA was 130° C. Thereafter, the reaction was continued for 4 hours, and the operation was performed while the catalyst layer outlet temperature was adjusted to be 130° C.

The whole amount of a solution from the start of the supply of 3 wt % CMHP/CUM/CMA until the stop of the supply was recovered. The weight of the recovered solution was 506 g.

HPO titration was performed for the recovered solution to find that the CMHP concentration was 0.06%.

2. Simple Distillation Step

In a flask, 490 g of the solution obtained through the epoxidation reaction step was charged. A Liebig condenser was connected to the flask in order to cool a solution to be distilled out, and a receiver for recovering the distillate was installed. The Liebig condenser temperature was set to −5° C. The flask in which the reaction solution had been charged was immersed in an oil bath and heated, and the temperature of the oil bath was increased until the temperature of the reaction solution reached 160° C. When the temperature reached 160° C., the temperature was retained for 20 minutes, and thereafter the flask was removed from the oil bath. The solution in the flask was naturally cooled, and thereafter the solution cooled to near the room temperature was recovered to find that the weight was 477 g. The proportion of the distillate to the charged solution was 2.7%.

3. Dehydration and Hydrogenation Step

A metal reactor (the metal reactor includes a sheath tube having an outer diameter of 3 mm, the sheath tube including a thermometer therein) having an inner diameter of 14 mm was filled with a catalyst (the mass of the catalyst was 3.0 g, and the catalyst contains alumina and 0.05% by mass of palladium). The catalyst holding method was a fixed bed.

Liquid cumene was supplied to the reactor to fill the reactor with the liquid cumene. Thereafter, the reactor was heated in an electric furnace in such a way that the inlet part temperature of the catalyst layer reached 220° C. while a nitrogen gas and liquid cumene were supplied to the reactor at 84 Nml/min and 24 g/hour respectively. After the inlet part temperature of the catalyst layer became stable at 220°

C., the nitrogen gas was switched to a hydrogen-containing gas to supply the hydrogen-containing gas at 72 Nml/min. The solution obtained through the simple distillation step was supplied as a raw material solution in place of liquid cumene to the reactor at 24 g/hour by switching the liquid supply lines substantially simultaneously with the switching to the hydrogen-containing gas. A liquid (reaction solution) discharged from the reactor between 165 to 180 minutes from the start of the supply of the hydrogen gas was recovered. The concentrations of cumyl alcohol and α-methylstyrene were analyzed by gas chromatography for each of the raw material solution and the reaction solution.

The conversion of cumyl alcohol and the conversion of α-methylstyrene, calculated from the cumyl alcohol concentrations and the α-methylstyrene concentrations in the raw material solution and the reaction solution, were 33% and 79% respectively. Table 2 shows the analysis results. Note that the average temperature of the catalyst layer, measured during recovering the reaction solution, was 224° C.

Note that the conversion of cumyl alcohol and the conversion of α-methylstyrene were calculated from the following equation (10) and equation (11).

$$\text{Conversion of cumyl alcohol} = \{(\text{cumyl alcohol concentration in raw material solution}) - (\text{cumyl alcohol concentration in reaction solution})\} / (\text{cumyl alcohol concentration in raw material solution}) \times 100 \quad (10)$$

$$\text{Conversion of } \alpha\text{-methylstyrene} = \{(\text{cumyl alcohol concentration in raw material solution}) - (\text{cumyl alcohol concentration in reaction solution}) + (\alpha\text{-methylstyrene concentration in raw material solution}) - (\alpha\text{-methylstyrene concentration in reaction solution})\} / \{(\text{cumyl alcohol concentration in raw material solution}) - (\text{cumyl alcohol concentration in reaction solution}) + (\alpha\text{-methylstyrene concentration in raw material solution})\} \times 100 \quad (11)$$

Test Example 2

1. Epoxidation Reaction Step

The titanosilicate in an amount of 3.5 g was used, and the reactor was filled with the titanosilicate under the same conditions as in Test Example 1.

Propylene was supplied at 0.8 g/min simultaneously with the start of heating the reactor in an electric furnace. The pressure in the reactor was increased by the supply of propylene, and PCV (flow valve) at the outlet was adjusted in such a way that the pressure became 6 MPa-G. The catalyst layer outlet temperature reached 40° C. 10 minutes later. Thereafter, the electric furnace temperature was adjusted in such a way that the catalyst layer outlet temperature was 40° C., and propylene was supplied for 405 minutes in total. The ratio of volume of propylene supplied at that time/volume of titanosilicate was 64.5. Except for those described above, the epoxidation reaction step was performed by the same method as in Test Example 1.

The weight of the recovered solution was 513 g.

HPO titration was performed for the recovered solution to find that the CMHP concentration was 0.14%.

2. Simple Distillation Step

In a flask, 485 g of the solution obtained through the epoxidation reaction step was charged. A Liebig condenser was connected to the flask in order to cool a solution to be distilled out, and a receiver for recovering the distillate was installed. The Liebig condenser temperature was set to −5° C. The flask in which the reaction solution had been charged was immersed in an oil bath and heated, and the temperature of the oil bath was increased until the temperature of the reaction solution reached 160° C. When the temperature reached 160° C., the temperature was retained for 15 minutes, and thereafter the flask was removed from the oil bath. The solution in the flask was naturally cooled, and thereafter the solution cooled to near the room temperature was recovered to find that the weight was 471 g. The proportion of the distillate to the charged solution was 2.9%.

3. Dehydration and Hydrogenation Step

The dehydration and hydrogenation step was performed under the same conditions as in Test Example 1. Then, a liquid (reaction solution) discharged from the reactor between 165 to 180 minutes from the start of the supply of the hydrogen gas was recovered. The concentrations of cumyl alcohol and α-methylstyrene in the raw material solution and the reaction solution were analyzed in the same manner as in Test Example 1. The conversion of cumyl alcohol and the conversion of α-methylstyrene, calculated from the cumyl alcohol concentrations and the α-methylstyrene concentrations in the raw material solution and the raw material solution, were 32% and 79% respectively. The average temperature of the catalyst layer, measured during recovering the reaction solution, was 225° C.

Test Example 3

1. Epoxidation Reaction Step

The titanosilicate in an amount of 3.6 g was used, and the reactor was filled with the titanosilicate under the same conditions as in Test Example 1.

Propylene was supplied at 0.8 g/min simultaneously with the start of heating the reactor in an electric furnace. The pressure in the reactor was increased by the supply of propylene, and PCV (flow valve) at the outlet was adjusted in such a way that the pressure became 6 MPa-G. When the propylene was supplied for 26 minutes, the catalyst layer outlet temperature reached 93° C. The ratio of volume of propylene supplied at that time/volume of titanosilicate was 4.1. Thereafter, 3 wt % CMHP/CUM/CMA was supplied at 2.25 g/min. The time when the supply of 3 wt % CMHP/CUM/CMA was started was defined as the start of the reaction 0 min.

At the time when 60 minutes elapsed from starting to supply 3 wt % CMHP/CUM/CMA, the catalyst layer outlet temperature was 130° C. The electric furnace temperature was adjusted in such a way that the catalyst layer outlet temperature was 130° C., and the reaction was performed for 4 h.

The whole amount of a solution from the start of supplying 3 wt % CMHP/CUM/CMA until the stop of the supply was recovered. The weight of the recovered solution was 540 g. HPO titration was performed for the recovered solution to find that the CMHP concentration was 0.08%.

2. Simple Distillation Step

In a flask, 519 g of the solution obtained through the epoxidation reaction step was charged. A Liebig condenser was connected to the flask in order to cool the solution distilled out, and a receiver for recovering the distillate was installed. The Liebig condenser temperature was set to −5°

C. The flask in which the reaction solution had been charged was immersed in an oil bath and heated, and the temperature of the oil bath was increased until the temperature of the reaction solution reached 161° C. When the temperature reached 161° C., the temperature was retained for 20 minutes, and thereafter the flask was removed from the oil bath. The solution in the flask was naturally cooled, and thereafter the solution cooled to near the room temperature was recovered to find that the weight was 507 g. The proportion of the distillate to the charged solution was 2.3%.

3. Dehydration and Hydrogenation Step

The dehydration and hydrogenation step was performed under the same conditions as in Test Example 1. Then, a liquid (reaction solution) discharged from the reactor between 165 to 180 minutes from the start of the supply of the hydrogen gas was recovered. The concentrations of cumyl alcohol and α-methylstyrene in the raw material solution and the reaction solution were analyzed in the same manner as in Test Example 1. The conversion of cumyl alcohol and the conversion of α-methylstyrene, calculated from the cumyl alcohol concentrations and the α-methylstyrene concentrations in the raw material solution and the raw material solution, were 27% and 64% respectively. The average temperature of the catalyst layer, measured during recovering the reaction solution, was 223° C.

TABLE 2

| | Test Example 1 | Test Example 2 | Test Example 3 |
|---|---|---|---|
| Conversion of cumyl alcohol | 33% | 32% | 27% |
| Conversion of α-methylstyrene | 79% | 79% | 64% |

CONCLUSION

The ratio of the total flow volume (β) of propylene supplied until the peroxide is supplied to the reactor to the volume (α) of the titanosilicate stored in the reactor, (β/α), in the epoxidation reaction step is "64.6" in Test Example 1, "64.5" in Test Example 2, and "4.1" in Test Example 3. As can be seen in Table 2 above, it is recognized that the conversion of cumyl alcohol and the conversion of α-methylstyrene are higher in Test Examples 1 and 2 than in Test Example 3. That is, by performing the epoxidation reaction step setting the ratio to 5 or more, the respective conversions in the dehydration and hydrogenation step can be improved.

REFERENCE SIGNS LIST

1: Reactor
1*a*: Supply part
1*b*: Discharge part
1*c*: Titanosilicate layer
2: Supply line
3: Discharge line
4: Connection line
5: Sampling mechanism
5*a*: Sampling line
5*b*: Sampling valve
5*c*: Sealing part
5*d*: Sealing valve
6: Switching mechanism
6*a*: Switching valve
10: Epoxidation reaction part
100: Production apparatus

The invention claimed is:

1. A propylene oxide production apparatus that produces propylene oxide by epoxidizing propylene using a peroxide in the presence of a titanosilicate, the apparatus comprising:

at least three reactors in which the titanosilicate is stored and to which propylene and the peroxide are supplied as reaction raw materials;

a supply line that supplies the reaction raw materials, which have not yet supplied to each reactor, to each reactor;

a discharge line that is connected to each reactor and that discharges a reaction mixture comprising propylene oxide from each reactor;

a switching mechanism that is capable of switching a state of each reactor between an operating state where the reaction raw materials are supplied and an epoxidation reaction is performed and a non-operating state where the supply of the reaction raw materials is shut off, that is capable of changing a reactor in the non-operating state one by one, and that performs switching in such a way that only reactors in the operating state are connected fluidically in series or in parallel, thereby enabling supplying the reaction raw materials to the reactors in the operating state; and a sampling mechanism that samples part of the reaction mixture from each discharge line that is connected to each reactor, wherein the propylene oxide production apparatus is configured to supply the reaction raw materials in order of propylene and subsequently the peroxide, and have a ratio of a total flow volume (β) of propylene supplied until the peroxide is supplied in the reactor switched from the non-operating state to the operating state to a volume (α) of the titanosilicate stored in the reactor switched from the non-operating state to the operating state, (β/α), being 5 to 6000.

2. The propylene oxide production apparatus according to claim 1, further comprising a connection line that connects reactors fluidically with each other and that supplies the reaction mixture that is discharged from one of the connected reactors to another reactor, the reaction mixture comprising the reaction raw materials, wherein the switching mechanism connects only the reactors in the operating state in series by the connection line or lines.

3. The propylene oxide production apparatus according to claim 1, wherein each reactor comprises: a supply part to which the reaction raw materials are supplied; and a discharge part from which the reaction mixture is discharged, and further comprises thermometers that measure internal temperatures of the supply part and the discharge part respectively.

4. The propylene oxide production apparatus according to claim 1, wherein each reactor comprises a titanosilicate layer formed by the stored titanosilicate, and further comprises a thermometer that measures an internal temperature of the titanosilicate layer.

5. The propylene oxide production apparatus according to claim 1, wherein each reactor comprises: a supply part to which the reaction raw materials are supplied; and a discharge part that discharges the reaction mixture, and further comprises pressure gauges that measure internal pressures of the supply part and the discharge part respectively.

6. The propylene oxide production apparatus according to claim 1, wherein the at least three reactors have approximately the same size.

7. The propylene oxide production apparatus according to claim 1, wherein each reactor has a cylindrical shape, and when an inner diameter of the reactor is assumed to be D (m) and a height of the reactor is assumed to be L (m), L/D is 0.5 to 20.

8. The propylene oxide production apparatus according to claim 1, wherein each reactor comprises a pressure release valve capable of releasing internal pressure.

9. The propylene oxide production apparatus according to claim 1, wherein the sampling mechanism comprises a sampling line that branches from each discharge line that is connected to each reactor, and that takes in part of the reaction mixture, and an inner dimeter of the sampling line is smaller than an inner diameter of the discharge line to which the sampling line is connected.

10. The propylene oxide production apparatus according to claim 9, wherein the sampling line comprises a sealing part capable of forming a tightly closed region to retain the reaction mixture and has a sampling port at the sealing part.

11. The propylene oxide production apparatus according to claim 1, wherein the titanosilicate is a silylated titanosilicate.

12. The propylene oxide production apparatus according to claim 11, wherein the titanosilicate is a titanosilicate silylated with 1,1,1,3,3,3-hexamethyldisilazane.

13. The propylene oxide production apparatus according to claim 1, wherein the peroxide is an organic peroxide.

14. The propylene oxide production apparatus according to claim 13, wherein the organic peroxide is at least one selected from the group consisting of cumene hydroperoxide, ethylbenzene hydroperoxide, and tert-butyl hydroperoxide.

15. A propylene oxide production method using the propylene oxide production apparatus according to claim 1 and comprising:

(1) a first step of exchanging the titanosilicate in the reactor in the non-operating state while supplying the reaction raw materials to the reactors in the operating state and performing the epoxidation;

(2) a second step of switching the reactor in the non-operating state, in which the titanosilicate has been exchanged, to the operating state and switching one or some reactors of a plurality of the reactors in the operating state to the non-operating state by the switching mechanism, and supplying the reaction raw materials to the reactors in the operating state and performing the epoxidation; and (3) a sampling step of sampling part of the reaction mixture by the sampling mechanism and checking a deactivation status of the titanosilicate, wherein the first step and the second step are repeated, and thereby the epoxidation is performed while the reactor to be placed in the non-operating state is changed one by one to exchange the titanosilicate, the second step comprises a first supply step of switching the reactor in the non-operating state, in which the titanosilicate has been exchanged, to the operating state and supplying the reaction raw materials in order of propylene and subsequently the peroxide, and in the first supply step, a ratio of a total flow volume (β) of propylene supplied until the peroxide is supplied in the reactor switched from the non-operating state to the operating state to a volume (α) of the titanosilicate stored in the reactor switched from the non-operating state to the operating state, (β/α), is 5 to 6000.

16. A propylene oxide production method using the propylene oxide production apparatus according to claim 2 and comprising:

(1) a first step of exchanging the titanosilicate in the reactor in the non-operating state while connecting only the reactors in the operating state in series by the connection line or lines and supplying the reaction raw materials to the reactors in the operating state and performing the epoxidation;

(2) a second step of switching the reactor in the non-operating state, in which the titanosilicate has been exchanged, to the operating state, switching one or some reactors of a plurality of the reactors in the operating state to the non-operating state, connecting only the reactors in the operating state in series by the connection line or lines, and supplying the reaction raw materials to the reactors in the operating state by the switching mechanism and performing the epoxidation; and (3) a sampling step of sampling part of the reaction mixture by the sampling mechanism and checking a deactivation status of the titanosilicate, wherein the first step and the second step are repeated, and thereby the epoxidation is performed while the reactor to be placed in the non-operating state is changed one by one to exchange the titanosilicate, the second step comprises a first supply step of switching the reactor in the non-operating state, in which the titanosilicate has been exchanged, to the operating state and supplying the reaction raw materials in order of propylene and subsequently the peroxide, and in the first supply step, a ratio of a total flow volume (β) of propylene supplied until the peroxide is supplied in the reactor switched from the non-operating state to the operating state to a volume (α) of the titanosilicate stored in the reactor switched from the non-operating state to the operating state, (β/α), is 5 to 6000.

17. The propylene oxide production method according to claim 15, wherein timing of switching one or some reactors to the non-operating state in the second step is determined according to the deactivation status of the titanosilicate.

18. The propylene oxide production method according to claim 15, further comprising a step of separating an alcohol from the reaction mixture.

19. The propylene oxide production method according to claim 15, wherein in the first supply step, a titanosilicate layer outlet temperature in the reactor is set to 40 to 150° C. when the peroxide has been supplied to the reactor and the reactor in the non-operating state has been switched to the operating state.

20. The propylene oxide production method according to claim 15, wherein in the first supply step, a titanosilicate layer outlet temperature in the reactor is set to 40 to 150° C. during supplying only propylene to the reactor.

* * * * *